(12) United States Patent
Mallard et al.

(10) Patent No.: US 8,709,392 B2
(45) Date of Patent: *Apr. 29, 2014

(54) COSMETIC/DERMATOLOGICAL COMPOSITIONS COMPRISING NAPHTHOIC ACID COMPOUNDS AND POLYURETHANE POLYMERS

(71) Applicant: Galderma Research & Development, Biot (FR)

(72) Inventors: Claire Mallard, Mougins (FR); Eve Ferrara, Valbonne (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/889,163

(22) Filed: May 7, 2013

(65) Prior Publication Data

US 2013/0245123 A1    Sep. 19, 2013

Related U.S. Application Data

(63) Continuation of application No. 13/171,872, filed on Jun. 29, 2011, now Pat. No. 8,435,502, which is a continuation of application No. 12/076,169, filed on Mar. 14, 2008, now Pat. No. 7,998,467, which is a continuation of application No. PCT/IB2006/003852, filed on Sep. 15, 2006.

(60) Provisional application No. 60/725,279, filed on Oct. 12, 2005.

(30) Foreign Application Priority Data

Sep. 16, 2005 (FR) ...................................... 05 09493

(51) Int. Cl.
*A61K 31/35* (2006.01)

(52) U.S. Cl.
USPC ...................................................... 424/78.03

(58) Field of Classification Search
None
See application file for complete search history.

(56) References Cited

U.S. PATENT DOCUMENTS

| 6,358,541 | B1 | 3/2002 | Goodman | |
|---|---|---|---|---|
| 7,998,467 | B2 * | 8/2011 | Mallard et al. | 424/78.03 |
| 8,435,502 | B2 * | 5/2013 | Mallard et al. | 424/78.03 |
| 2002/0155180 | A1 | 10/2002 | Goodman | |
| 2008/0181963 | A1 | 7/2008 | Orsoni et al. | |

FOREIGN PATENT DOCUMENTS

| EP | 0299758 A2 | 1/1989 |
|---|---|---|
| WO | WO 03/075908 A1 | 9/2003 |

OTHER PUBLICATIONS

Kang et al., "Assessment of adapalene gel for the treatment of actinic keratoses and lentigines: A randomized trial", J. Am. Acad. Dermatol., Jul. 2003, pp. 83-90, vol. 49, No. 1.
Database WPI, Section Ch, Week 199406 Derwent Publications, Ltd. London, GB, Class A60, AN 1994-045515, abstract of JP 06 001851A (Toyo Ink Mfg Co), Jan. 11, 1994.

(Continued)

*Primary Examiner* — Anand Desai
*Assistant Examiner* — Melissa Mercier
(74) *Attorney, Agent, or Firm* — Dentons US LLP

(57) ABSTRACT

Cosmetic/dermatological compositions for topical application and useful for the treatment, e.g., of acne, contain, formulated into a physiologically acceptable medium, at least one naphthoic acid compound and at least one polyurethane polymer or derivative thereof, the at least one naphthoic acid compound being dispersed therein.

30 Claims, 8 Drawing Sheets

(56) References Cited

OTHER PUBLICATIONS

Wolf, *Journal of the European Academy of Dermatology and Venereology*, "An update of recent clinical trials examining adapalene and acne", vol. 15, No. SUPP3, 2001, pp. 23-29, U.K.

International Search Report for corresponding PCT/IB2006/003852 dated Jun. 5, 2007.
International Preliminary Report on Patentability for corresponding PCT/IB2006/003852 dated Mar. 18, 2008.

* cited by examiner

COSMETIC/DERMATOLOGICAL COMPOSITIONS COMPRISING NAPHTHOIC ACID COMPOUNDS AND POLYURETHANE POLYMERS

CROSS-REFERENCE TO EARLIER APPLICATIONS

This application is a continuation of U.S. application Ser. No. 13/171,872, filed on Jun. 29, 2011, now U.S. Pat. No. 8,435,502, which is a continuation of U.S. application Ser. No. 12/076,169, filed Mar. 14, 2008, now U.S. Pat. No. 7,998,467, issued Aug. 16, 2011, which is a continuation of PCT/IB2006/003852, filed Sep. 15, 2006 and designating the United States, published in the English language as WO 2007/031883 A2 on Mar. 22, 2007, which claims benefit of U.S. Provisional Application No. 60/725,279, filed Oct. 12, 2005 and also claims foreign priority of FR 0509493, filed Sep. 16, 2005, each hereby expressly incorporated by reference in its entirety and each assigned to the assignee hereof.

BACKGROUND OF THE INVENTION

1. Technical Field of the Invention

The present invention relates to novel compositions for topical application, to processes for preparing such compositions and to the administration thereof as cosmetic or pharmaceutical products, said compositions being particularly useful for treating acne.

2. Description of Background and/or Related and/or Prior Art

Acne is a common multi-factor pathology that attacks skin rich in sebaceous glands (face, shoulder area, arms and intertriginal areas). It is the most commonly occurring form of dermatosis. The following five pathogenic factors play a determining role in the formation of acne:

1. genetic predisposition;
2. overproduction of sebum (seborrhoea);
3. androgens;
4. follicular keratinization disorders (comedogenesis); and
5. bacterial colonization and inflammatory factors.

There are several forms of acne, the common factor of all being attack of the pilosebaceous follicles. Especially exemplary are acne conglobata, cheloid acne of the nape of the neck, medication-related acne, recurrent miliary acne, necrotic acne, neonatal acne, premenstrual acne, occupational acne, acne rosacea, senile acne, solar acne and simple acne.

Simple acne, also known as polymorphic juvenile acne, is the most common. It comprises four stages, but passage through all the stages is not obligatory:

stage 1 corresponds to comedonic acne characterized by a large number of open and/or closed comedones and of microcysts;

stage 2, or papulopustular acne, is of mild to moderate seriousness. It is characterized by the presence of open and/or closed comedones, microcysts, but also red papules and pustules. It mainly affects the face and leaves few scars;

stage 3, or papulocomedonic acne, is more serious and extends to the back, the chest and the shoulders. It is accompanied by a larger number of scars;

stage 4, or nodulocystic acne, is accompanied by many scars. It presents nodules and also painful voluminous crimson pustules.

The various forms of acne described above may be treated with active agents such as anti-seborrhoeic agents and anti-infectious agents, for example benzoyl peroxide (especially the product Eclaran® marketed by Pierre Fabre), with retinoids such as tretinoin (especially the product Retacnyl® marketed by Galderma) or isotretinoin (the product Roaccutane® marketed by Laboratoires Roche), or with naphthoic acid derivatives. Naphthoic acid derivatives such as, especially, 6-[3-(1-adamantyl)-4-methoxyphenyl]-2-naphthoic acid, which is commonly known as adapalene (the product Differine® marketed by Galderma), are widely described and acknowledged as active principles that are just as effective as tretinoin for the treatment of acne. Adapalene also has the advantage of causing fewer side effects, such as phenomena of irritation, dryness of the skin or intolerance, than the other active agents described above, which makes it a product of choice.

Too, need exists to develop compositions for increasing the topical penetration of certain active agents by including, in compositions, compounds of polyurethane polymer type or derivatives thereof (EP-0,299,758). The product Avita®, marketed by Bertek Pharmaceuticals Inc., is an example thereof. It especially contains 0.025% by weight, relative to the total weight of the composition, of tretinoin dissolved in compositions of cream or gel type and containing polyurethane polymers (type-2 polyolprepolymers marketed by Bertek Pharmaceuticals Inc.) to limit desquamation, irritation and dryness of the skin.

The U.S. Patent Publication Application No. 2002/01555180 describes a composition comprising as active principle an Extract of Saw Palmetto Berries (SPBE), and in which adapalene is used as an agent for improving the penetration of the active principle SPBE into the follicles and the sebaceous gland.

SUMMARY OF THE INVENTION

It has now been demonstrated, surprisingly, that polyurethane polymers, which are known to increase the topical penetration of only certain dissolved active agents (absence of crystals of these active agents when observed by microscope), can also promote the topical penetration of insoluble compounds, dispersed or suspended in pharmaceutical compositions, especially the naphthoic acid compounds.

However, nothing in the prior art would suggest that the anti-irritant effect of polyurethane polymers could be obtained with an active agent in dispersed and undissolved form.

Taking the foregoing into account, the present invention features preparing stable compositions that are less irritant than those of the prior art, comprising at least one naphthoic acid derivative in dispersed form and at least one compound of polyurethane polymer type or derivatives thereof, and also a process for preparing such a composition; said composition promoting the topical penetration of the active principle in dispersed form.

Thus, a first embodiment of the invention features compositions for topical application, comprising, formulated into a physiologically acceptable medium, at least one naphthoic acid derivative and at least one compound of polyurethane polymer type or derivatives thereof, the said naphthoic acid derivative being in dispersed form in the said composition, the said composition not comprising any extract of saw palmetto berries.

According to the present invention, the term "active agent in dispersed form" means an active principle in the form of solid particles, suspended in a given vehicle. Such particles are especially greater than 10 µm in size.

A second embodiment of the invention is a process for preparing a composition for topical application, which comprises the step of mixing a physiologically acceptable vehicle containing at least one naphthoic acid derivative with at least one compound of polyurethane polymer type or derivatives thereof, the said naphthoic acid derivative being in a form dispersed in the said composition. The term "physiologically acceptable vehicle" means a vehicle that is compatible with the skin, mucous membranes and/or the integuments.

Finally, a third embodiment of the invention features the administration of a composition as described above, formulated as a pharmaceutical composition, for treating and/or preventing dermatological complaints/afflictions associated with a keratinization disorder that has a bearing on cell differentiation and proliferation, especially for treating comedonic acne, simple acne, papulocomedonic acne, nodulocystic acne, polymorphic acne, acne rosacea, acne conglobata, senile acne, and secondary acnes such as solar acne, medication-related acne or occupational acne.

When such a composition comprises, in a physiologically acceptable medium, at least one naphthoic acid derivative and at least one compound of polyurethane polymer type or derivatives thereof, the naphthoic acid derivative being in a form dispersed in the said composition, it exhibits good chemical stability, high anti-comedolytic efficacy and also good tolerance.

The invention will be understood more clearly from the description that follows, with reference to the attached figures of drawings.

Figure 1:
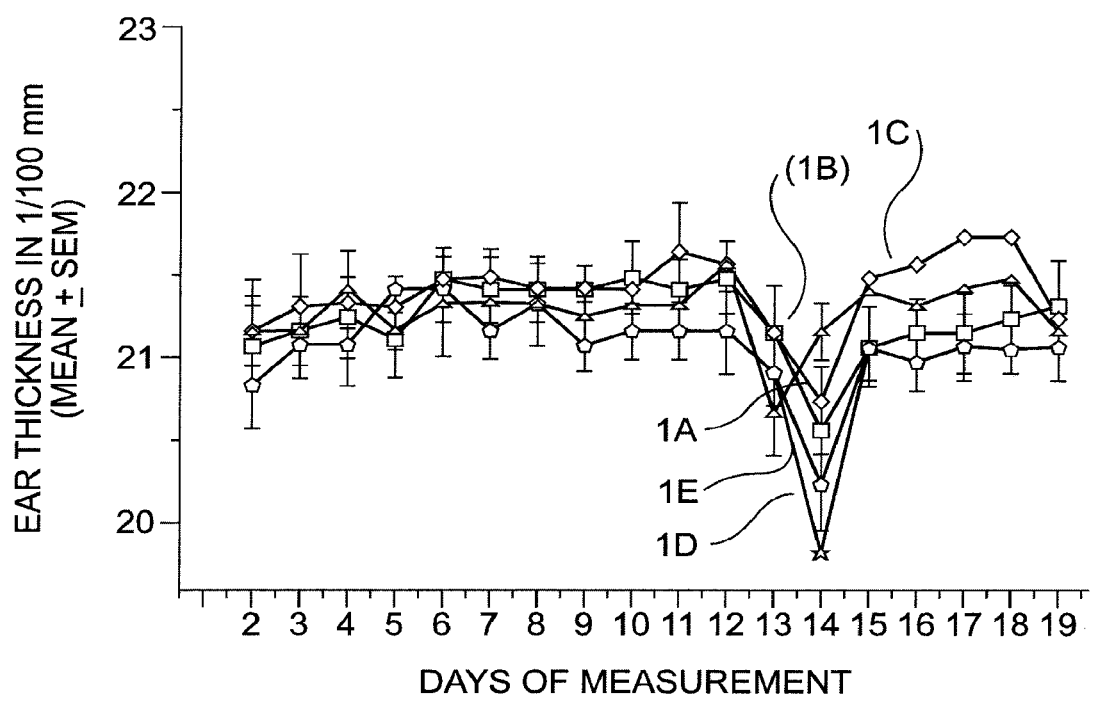
FIGS. 1 to 4 show the results of a study form comparing the irritant power of a reference gel containing 0.1% adapalene with that of three 0.1% adapalene formulations in gel form comprising a polyurethane polymer at various concentrations, and also placebos thereof, on the skin of BALB/c mouse ear after repeated topical applications for 6 days.

DETAILED DESCRIPTION OF BEST MODE AND SPECIFIC/PREFERRED EMBODIMENTS OF THE INVENTION

The compositions according to the invention comprise at least one naphthoic acid compound and at least one compound of polyurethane polymer type or derivatives thereof.

Naphthoic acid is a compound having the formula:

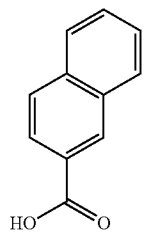

The term "naphthoic acid derivative" or "compound" means the compounds of formula (I):

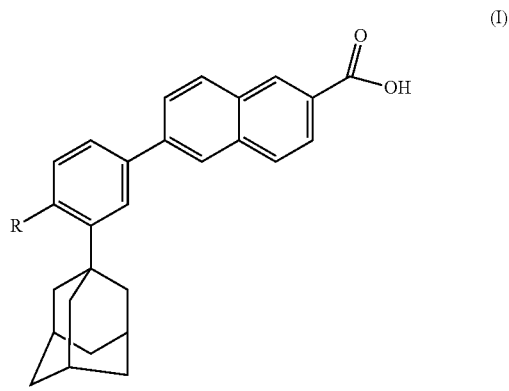

in which R is a hydrogen atom, a hydroxyl radical, a branched or unbranched alkyl radical having from 1 to 4 carbon atoms, an alkoxy radical having from 1 to 10 carbon atoms or a substituted or unsubstituted cycloaliphatic radical.

The term "linear or branched alkyl radical having from 1 to 4 carbon atoms" preferably means methyl, ethyl, propyl and butyl radicals.

The term "alkoxy radical having from 1 to 10 carbon atoms" preferably means methoxy, ethoxy, propoxy, butoxy, hexyloxy and decyloxy radicals.

The term "cycloaliphatic radical" preferably means monocyclic or polycyclic radicals such as the 1-methylcyclohexyl radical or the 1-adamantyl radical.

Among the naphthoic acid derivatives that may be included in the compositions according to the invention, 6-[3-(1-adamantyl)-4-methoxyphenyl]-2-naphthoic acid (adapalene), 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid will advantageously be selected.

The abovementioned naphthoic acid derivatives are generally in a form dispersed in the compositions according to the invention. The insoluble naphthoic acid derivatives are thus uniformly distributed in the compositions according to the invention.

In the compositions according to the invention, the naphthoic acid derivatives are included at concentrations of less than or equal to 10% by weight relative to the total weight of the composition, and preferably from 0.001% to 10% by weight relative to the total weight of the composition, preferentially from 0.01% to 5%, more preferentially from 0.05% to 2% to most preferentially from 0.1% to 0.3% by weight relative to the total weight of the composition. Throughout the present text, unless otherwise specified, it should be understood that when ranges of concentrations are given, the upper and lower limits of the said range are included.

Advantageously, the naphthoic acid derivative in the compositions according to the invention is adapalene. The adapalene concentration in the compositions according to the invention is then from 0.01% to 0.5%, and preferentially equal to 0.03%, more preferentially from 0.1% to 0.3% to in particular at a concentration of 0.1% to at a concentration of 0.3%.

Preferably, the naphthoic acid derivative(s) is (are) the only active principle(s) present in the compositions according to the invention. Preferentially adapalene is the only active principle in the composition.

The compositions according to the invention also comprise compounds of polyurethane polymer type or derivatives thereof. The term "polyurethane polymers" especially means polyalkylene glycols as described in EP-0,299,758, and marketed by Bertek Pharmaceuticals Inc. The polyurethane polymers according to the invention have unique properties that impart to them advantageous properties for applications in cosmetics and pharmaceuticals. Specifically, polyurethane polymers significantly influence the deposition of certain agents onto and into the skin, by virtue of their high molecular weight. Moreover, polyurethane polymers preferentially remain in the upper layers of the skin.

Among the polyurethane polymers that may be included in the compositions according to the invention, exemplary are the polyurethane polymers of general formula:

action on the skin. It is thus advantageous to reduce the irritation induced in order to be able to increase the doses.

The compositions of the present invention may be in any galenical form normally used for topical application, whether regime or regimen, especially in the form of aqueous, aqueous-alcoholic or oily dispersions, dispersions of the lotion type, aqueous, anhydrous or lipophilic gels, emulsions of liquid or semi-liquid consistency of the milk type, obtained by dispersing a fatty phase in an aqueous phase (O/W) or vice versa (W/O), or suspensions or emulsions of soft, semi-liquid or solid consistency of the cream, cream-gel or pomade type, or, alternatively, microemulsions, microcapsules, microparticles or vesicular dispersions of ionic and/or nonionic type.

Preferably, the compositions according to the invention are in the form of lotions, cream-gels, gels or creams.

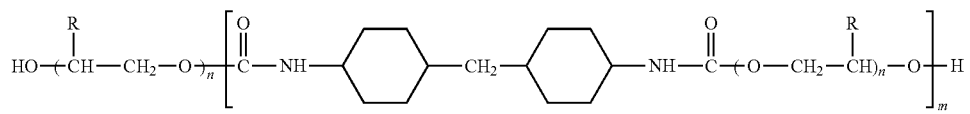

in which:

R is CH$_3$ or H;

n is an integer selected such that the polyurethane polymer has a molecular mass at least equal to 1,000, and n advantageously ranges from 5 to 55;

and m is a number ranging from 1 to 6, inclusive.

Examples of polyurethane polymers that may be included in the compositions according to the invention include polyolprepolymer-2 (PP-2) and polyolprepolymer-14 (PP-14) (named poly[oxy(methyl-1,2-ethanediyl)], α-hydro-ω-hydroxy-, polymer with 1,1'-methylenebis[4-isocyanatocyclohexane]), and polyolprepolymer-15 (PP-15) (named poly (oxy-1,2-ethanediyl), α-hydro-ω-hydroxy-, polymer with 1,1'-methylenebis[4-isocyanatocyclohexane]), taken alone or as a mixture. These three polymers are marketed by Bertek Pharmaceuticals Inc., and correspond to the general formula above with m ranging from 1 to 4 and for which, respectively, n=12 for PP-2, n=51 for PP-14 and n=8 for PP-15.

Among the polyurethane polymers that may be included in the compositions according to the invention, polyolprepolymer-2 (PP-2) will advantageously be selected.

In the compositions according to the invention, the compounds of polyurethane polymer type or derivatives thereof are included at concentrations of less than or equal to 20% to preferably from 0.5% to 20% by weight, more preferentially from 1% to 10% by weight and in particular 1%, 3%, 7% or 10% by weight relative to the total weight of the composition, and preferentially at a concentration lower than or equal to 7%. Such low concentrations of polyurethane polymers advantageously make it possible to reduce the toxicity and the general irritation of the compositions according to the invention.

The presence of polyurethane polymers in the compositions according to the invention, which are deposited in the stratum corneum, allows the formation of a reservoir in the upper part of the skin. This reservoir allows the naphthoic acid derivatives to be released gradually into the deeper layers of the epidermis. In addition, it has been noted, surprisingly, that the polyurethane polymers contained in the compositions according to the invention have anti-irritant and moisturizing properties that may be particularly advantageous in the case of adapalene formulations. The reason for this is that naphthoic acid derivatives may be irritant and have a dehydrating One skilled in the art will take care to select the excipients constituting the compositions according to the invention as a function of the desired galenical form and such that the advantageous properties of the composition according to the invention are preserved.

The compositions according to the invention may also especially comprise one or more of the following ingredients:
a) one or more gelling agents or suspending agents,
b) one or more chelating agents,
c) one or more wetting agents,
d) one or more preservatives.

Examples of gelling agents or suspending agents that may be included in the compositions according to the invention are the carbomers marketed under the generic name Carbopol®, the "electrolyte-insensitive" carbomers marketed under the trademark Ultrez 10® or Carbopol ETD® by BF Goodrich, polysaccharides, examples of which include xanthan gum such as Keltrol T® marketed by Kelco, guar gum, chitosans, cellulose and derivatives thereof such as hydroxyethylcellulose, in particular the product marketed under the trademark Natrosol HHX 250® by Aqualon, and the copolymer of acrylamide and of sodium acrylamino-2-methylpropanesulfonate as a 40% dispersion in isohexadecane and polysorbate 80 marketed under the trademark Simulgel 600® by SEPPIC.

Preferred gelling agents are the carbomers marketed especially under the trademarks Carbopol 974P NF and Carbopol 980 NF.

Among the chelating agents, examples thereof include ethylenediaminetetraacetic acid (EDTA), diethylenetriaminepentaacetic acid (DTPA), ethylenediaminebis(O-hydroxyphenylacetic acid) (EDBHA), hydroxy-2-ethylenediaminetriacetic acid (HEDTA), ethyldiaminebis(O-hydroxy-p-methylphenyl)acetic acid (EDBHMA) and ethylenediaminebis(5-carboxy-2-hydroxyphenyl)acetic acid (EDBCHA).

A preferred chelating agent is ethylenediaminetetraacetic acid (EDTA) marketed especially under the trademark Titriplex III®.

Among the wetting agents, the role of which is to reduce the surface tension and to allow greater spreading of the liquid, compounds such as propylene glycol, dipropylene glycol, propylene glycol dipelargonate, lauroglycol and ethoxydiglycol, alone or as a mixture, are preferentially used, without this list being limiting.

A preferred wetting agent is propylene glycol.

Among the preservatives, examples thereof include benzoic acid and derivatives thereof with benzyl alcohol, benzalkonium chloride, sodium benzoate, bronopol, chlorhexidine, chlorocresol and derivatives thereof, ethyl alcohol, phenethyl alcohol, phenoxyethanol, potassium sorbate, diazolidinylurea, parabens such as propyl paraben or methyl paraben, taken alone or as mixtures.

Preferred preservatives include parabens and phenoxyethanol or benzalkonium chloride, alone or as a mixture.

The compositions according to the invention may comprise one or more emulsifiers.

Surfactant emulsifiers are amphiphilic compounds containing a hydrophobic portion with affinity for oil and a hydrophilic portion with affinity for water, thus creating a bond from the two phases. Ionic or nonionic emulsifiers thus stabilize oil/water emulsions by becoming adsorbed at the interface and by forming lamellar liquid crystal layers.

The emulsifying power of nonionic surfactants is closely linked to the polarity of the molecule. This polarity is defined by the HLB (hydrophilic/lipophilic balance).

A high HLB indicates that the hydrophilic fraction is predominant and, conversely, a low HLB indicates that the lipophilic portion is predominant. For example, HLB values of greater than about 10 correspond to hydrophilic surfactants.

Surfactants may be classified, according to their structure, under the generic terms "ionic" (anionic, cationic or amphoteric) or "nonionic". Nonionic surfactants are surfactants that do not dissociate into ions in water and are thus insensitive to pH variations.

Nonionic surfactants are particularly suitable for preparing emulsions of oil-in-water type, which are the subject of the present invention. Thus, the emulsifying system of which the emulsion of the invention is composed comprises at least one nonionic surfactant, with a hydrophilic predominant fraction, i.e., with a high HLB value, of greater than about 10.

Examples of nonionic surfactants with a high HLB value include sorbitan esters such as POE(20) sorbitan monooleate, marketed under the trademark "Tween 80" (HLB=15); POE(20) sorbitan monostearate marketed under the trademark "Tween 60" (HLB=14.9); fatty alcohol ethers such as POE(21) stearyl ether (HLB=15.5) or ceteareth 20 marketed under the trademark "Eumulgin B2" by Cognis (HLB=15.5); polyoxyethylene-polyoxypropylene block copolymers such as Synperonic PE/L44.

Preferably, the said high-HLB nonionic surfactants have an HLB of from 10 to 18.

Examples of low-HLB (lipophilic) nonionic surfactants include sorbitan esters, such as sorbitan monostearate (marketed under the trademark Span 60 by Unichema), glycerol esters (marketed under the trademark Cutina GMSVPH by Cognis) such as glyceryl monostearate (Cutina GMS from Cognis), Speziol C18 pharma, olipal isostearic (from gatefosse) and low-HLB sucrose esters, for instance sucrose distearate.

Preferably, the said low-HLB nonionic surfactants have an HLB of less than 10.

The nonionic surfactants may be used alone or as a mixture of two or more of them to form the emulsifying system of which the emulsion of the invention is composed.

Preferably, one or more high-HLB nonionic surfactant/low-HLB nonionic surfactant pairs will be used as emulsifying system: it may in particular be a nonionic emulsifying system comprising at least one nonionic surfactant with an HLB of greater than about 10 and at least one nonionic surfactant with an HLB of less than about 10.

The ratio of each of the two surfactants forming the above-mentioned pair is usually determined by calculating the required HLB of the fatty phase used.

Preferred emulsifiers include hydrophilic emulsifiers such as Tween 80, glyceryl stearate & PEG-100 stearate marketed under the trademark Arlacel 165FL® by Uniqema; PEG 6 stearate and PEG 32 stearate marketed under the trademark Tefose 1500 by Gattefosse, lipophilic emulsifiers such as Glucate SS (methyl glucose sesquistearate) and Glucamate SSE 20 (PEG 20 methyl glucose sesquistearate) marketed by Amerchol, polyoxyethylene (21) stearyl ether marketed under the trademark Brij721® by Uniqema, Eumulgin B2PH, and acrylates/C10-30 alkyl acrylate crosspolymer marketed under the trademark Pemulen TR1 by Noveon.

The compositions according to the invention may also comprise a fatty phase. This fatty phase may comprise, for example, plant oils, mineral oils, animal oils, synthetic oils or silicone oils, and mixtures thereof.

Examples of mineral oils include liquid paraffins of various viscosities such as Primol 352®, Marcol 82® and Marcol 152® marketed by Esso.

Plant oils that are exemplary include sweet almond oil, palm oil, soybean oil, sesame seed oil and sunflower oil.

Animal oils that are exemplary include lanolin, squalene, fish oil, mink oil with, as a derivative, squalane marketed under the trademark Cosbiol® by Laserson.

Synthetic oils that are exemplary include esters such as cetearyl isononanoate, for instance the product marketed under the trademark Cetiol SN® by Cognis France, diisopropyl adipate, for instance the product marketed under the trademark Ceraphyl 230® by ISF, isopropyl palmitate, for instance the product marketed under the trademark Crodamol IPP® by Croda, isopropyl adipate, for instance the product marketed under the trademark Crodamol DA by Croda and caprylic/capric triglyceride such as Miglyol 812® marketed by Hüls/Lambert Rivière.

Silicone oils that are exemplary include a dimethicone, for instance the product marketed under the trademark Dow Corning 200 Fluid®, a cyclomethicone, for instance the product marketed under the trademark Dow Corning 244 Fluid® by Dow Corning or the product marketed under the trademark Mirasil CM5® by SACI-CFPA.

Solid fatty substances such as natural or synthetic waxes may also be used. In this case, one skilled in the art will adapt the heating temperature of the preparation as a function of the presence or absence of these solids.

For the compositions according to the invention, liquid paraffins and more particularly Marcol 152® and Miglyol 812® are preferred.

The compositions of the invention may also comprise any additive usually used in cosmetics or pharmaceuticals, such as surfactants, neutralizers, sunscreens, antioxidants, fillers, electrolytes, dyes, common mineral or organic acids or bases, fragrances, essential oils, cosmetic active agents, moisturizers, vitamins, sphingolipids, self-tanning compounds such as DHA, calmatives and skin-protecting agents such as allantoin, and pro-penetrating agents, or a mixture thereof. In particular, the compositions according to the invention do not comprise any of the following active agents: glycolic acid, salicylic acid, retinol, tretinoin, retinaldehyde, azelaic acid and tazarotene.

Needless to say, one skilled in the art will take care to select this or these optional additional compound(s), and/or the amount thereof, such that the advantageous properties of the composition according to the invention are not, or are not substantially, adversely affected.

These additives may be present in the composition in a proportion of from 0.001% to 20% by weight relative to the total weight of the composition.

In one particular embodiment of the invention, the composition is in the form of an oil-in-water (O/W) emulsion of lotion, cream or cream-gel type and comprises:
from 0.1% to 0.3% of a naphthoic acid derivative;
from 1% to 10% of one or more polyurethane polymers or derivatives;
from 0.1% to 3% of gelling agents or suspending agents;
from 0.01% to 1.5% of chelating agents;
from 0.1% to 10% of a wetting agent;
from 0.1% to 20% of an emollient;
from 0.1% to 30% of fatty phase;
from 0.01% to 3% of preservatives;
from 0 to 10% of emulsifiers.

In another particular embodiment of the invention, the composition is in gel form and comprises:
from 0.1% to 0.3% of a naphthoic acid derivative;
from 1% to 10% of one or more polyurethane polymers or derivatives;
from 0.1% to 3% of gelling agents;
from 0.01% to 1.5% of chelating agents;
from 1% to 10% of a wetting agent;
from 0.01% to 3% of preservatives.

In yet another particular embodiment of the invention, the composition is in lotion form and comprises, in water:
from 0.1% to 0.3% of a naptoic acid derivative;
3% of one or more polyurethane polymers or derivatives, preferentially the polyolprepolymer of type 2;
0.2% of gelling agents or suspending agents;
0.1% of chelating agents;
from 2% to 6% to preferentially 4% of a wetting agent;
from 0.1% to 20% of an emollient;
7% of fatty phase;
from 1% to 1.5% of preservatives;
from 4% to 6% of emulsifiers.

The present invention also features administration of the compositions as described above, as medicaments.

This invention also features a process for preparing a composition as described above. Such a process comprises the step of mixing a physiologically acceptable vehicle comprising at least one naphthoic acid derivative with at least one compound of polyurethane polymer type or derivatives thereof, the said naphthoic acid derivative being in a form dispersed in the said composition.

The other possible excipients and additives will be introduced as a function of the chemical nature of the compounds and of the selected galenical form.

The preparation of a composition according to the invention is carried out in 2 or 4 steps according to the selected galenical form, the 2 additional steps being performed solely for the preparation of forms of emulsion type, such as creams, lotions or cream-gels.

The introduction of the polyolprepolymer into one or other of the steps is dependent on the lipophilic or hydrophilic nature of the polyolprepolymer. Thus, the polyolprepolymer of the type PP-2 of lipophilic nature is introduced into the fatty phase for the emulsions and after the neutralization step for the gels. The polyolprepolymer of the type PP-15, which is hydrophilic, is introduced into the active aqueous phase after dispersing of the gelling agent(s).

The preparation of a composition according to the invention is thus carried out according to the following process:
a) the naphthoic acid derivative is mixed with at least one wetting agent, at least one chelating agent, at least one gelling agent, optionally hydrophilic emulsifiers and emollients, in water, until the said naphthoic acid derivative is fully dispersed, in order to obtain the aqueous active phase;
b) optionally, to produce an emulsion, at least lipophilic emulsifiers, oils and/or solid fatty substances are mixed with preservatives, in order to obtain the fatty phase;
c) optionally, the said fatty phase obtained in b) is introduced into the aqueous active phase obtained in a) in order to obtain an emulsion;
d) if necessary, a gelling-agent neutralizer is introduced into the emulsion obtained in c) or into the aqueous phase obtained in a) in order to obtain the desired pH, and the remaining amount of water is added; the compound of polyurethane polymer type or derivatives thereof being introduced into the aqueous active phase obtained in a) or into the fatty phase obtained in step b) or during step d) as a function of its lipophilic or hydrophilic nature.

More specifically, the process for preparing the compositions according to the invention comprises the following steps:

Step a: Preparation of the Aqueous Active Phase:

Purified water, the active principle (adapalene), optionally the hydrophilic emulsifiers (such as Arlacel 165FL or Tween 80) in the case of preparing an oil-in-water emulsion, the emollients (such as glycerol or propylene glycol), the wetting agents (such as Synperonic PE/L62 or Synperonic PE/L44), the chelating agent (such as EDTA), the gelling agent(s) (such as Carbopol, Pemulen TR1, Xantural, Methocel or Simulgel 600) are introduced with stirring using a deflocculator into a beaker that will serve as the receiver for the finished product. The mixture is stirred without heating until fully dispersed. When the mixture is homogeneous, the aqueous phase is adjusted to 60° C. on a water bath and the preservative (such as methyl paraben) is introduced.

Step b (Optional): Preparation of the Fatty Phase:

The lipophilic emulsifiers (such as Glucate SS, Glucamate SSE 20 or Brij 721, Tefose 1500, Eumulgin B2 PH), the oily compounds (such as isostearic olepal, Cetiol SN, Crodamol DA, Speziol C18, Miglyol 812 or Cosbiol) and the preservatives (such as phenoxyethanol and propyl paraben) are introduced with stirring using a deflocculator into an additional beaker. The mixture is adjusted to 60° C. on a water bath and, after homogenization, the volatile silicone, if present, is introduced into the composition.

Step c (Optional): Emulsification:

The fatty phase is introduced gently into the aqueous phase at a temperature of 60° C. and with stirring using a deflocculator, in order to perform the emulsification. Heating is maintained for 5 minutes and the hotplate is then removed to allow the product to cool gently. The stirring is adjusted as a function of the viscosity.

Steps 2 and 3 are optional and are carried out solely for the preparation of forms of emulsion type such as creams, lotions or cream-gels.

Step d: Neutralization:

The gelling-agent neutralizer (such as triethanolamine or 10% sodium hydroxide solution) is introduced, if necessary, at 40° C., up to a pH of 5.5±0.5. The product then has a thicker consistency. At the end of the preparation, the pH is again checked. If it is within the norms, the sufficient quantity of water is added. The product is homogenized a final time in order to ensure good dispersion of the adapalene active principle (observation by microscope revealing a uniform dispersion free of aggregates), and the product is then packaged.

The compound of polyurethane polymer type is preferably a polyolprepolymer that is introduced during step a) (for the gel or emulsion formulations comprising a hydrophilic polymer) or during step b) (for the emulsion formulations comprising a lipophilic polymer), or during step d) (for the gel formulations comprising a lipophilic polymer) as a function of its lipophilic or hydrophilic nature.

The present invention also features the use of the novel compositions as described above in cosmetic and dermatology applications.

In particular, this invention features the administration of compositions as described above for pharmaceutical applications, whether regime or regimen, for treating and/or preventing dermatological conditions/afflictions associated with a keratinization disorder that has an influence on cell differentiation and proliferation, especially for treating simple acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne and medication-related acne.

More particularly, the present invention features the administration of compositions as described above for preventing or treating simple acne.

The said compositions according to the invention are preferentially administered topically.

In addition, this invention also features the cosmetic administration of a composition according to the invention for the treatment of acne-prone skin, for combating the greasy appearance of the skin or the hair, in the protection against the harmful aspects of sunlight or in the treatment of physiologically greasy skin, or for preventing and/or combating light-induced or chronological aging.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Production of a Formulation of Gel Type Containing Adapalene and Polyurethane Polymer The process is carried out in 4 steps:

Step 1: Preparation of the Aqueous Phase:

Purified water, EDTA and methyl paraben are introduced into a beaker. The beaker is then placed on a water bath (or on a hotplate) in order to adjust the solution to 80° C.±5° C., allowing dissolution of the paraben. Next, the beaker is stirred with a Rayneri blender equipped with a deflocculating paddle until totally dispersed. Carbopol 980 NF is then added as a shower and the mixture is stirred until fully dispersed.

Step 2: Preparation of the Active Phase:

Propylene glycol and Synperonic PE/L62 are introduced into an additional beaker. Adapalene is then introduced and the beaker is stirred using an Ultra-Turrax blender (paddle: 540 rpm; turbomixer 20 500 rpm). When the adapalene is fully dispersed (observation by microscope revealing a uniform dispersion free of aggregates), the phase is then added to the remainder of the formulation.

Step 3: Neutralization:

A sufficient amount of aqueous 10% (m/m) sodium hydroxide solution is added to the formula phase in order to adjust the formulation to pH 5.5±0.5.

Step 4: The Polyurethane Polymer (Polyolprepolymer-2) is Introduced:

The mixture is made up to the required volume with a sufficient quantity of water.

Example 2

Formulation of Gel Type Containing 0.1% Adapalene and Polyolprepolymer-2

The formula is prepared according to the procedure described in Example 1.

| Constituents | Content (% m/m) |
|---|---|
| Purified water | 80.00 |
| Na2 EDTA | 0.10 |
| Methyl paraben | 0.10 |
| Carbopol 980 NF | 1.00 |
| Propylene glycol | 4.00 |
| Synperonic PE/L62 | 0.20 |
| Adapalene | 0.10 |
| Polyolprepolymer-2 | 1.00 |
| 10% sodium hydroxide solution | qs pH 5.5 ± 0.5 |
| Purified water | qs 100 |

Example 3

Formulation of Gel Type Containing 0.1% Adapalene and Polyolprepolymer-2

The formula is prepared according to the procedure described in Example 1.

| Constituents | Content (% m/m) |
|---|---|
| Purified water | 80.00 |
| Na2 EDTA | 0.10 |
| Methyl paraben | 0.10 |
| Carbopol 980 NF | 1.00 |
| Propylene glycol | 4.00 |
| Synperonic PE/L62 | 0.20 |
| Adapalene | 0.10 |
| Polyolprepolymer-2 | 3.00 |
| 10% sodium hydroxide solution | qs pH 5.5 ± 0.5 |
| Purified water | qs 100 |

Example 4

Formulation of Gel Type Containing 0.1% Adapalene and Polyolprepolymer-2

The formula is prepared according to the procedure described in Example 1.

| Constituents | Content (% m/m) |
|---|---|
| Purified water | 80.00 |
| Na2 EDTA | 0.10 |
| Methyl paraben | 0.10 |
| Carbopol 980 NF | 1.00 |
| Propylene glycol | 4.00 |
| Synperonic PE/L62 | 0.20 |
| Adapalene | 0.10 |

-continued

| Constituents | Content (% m/m) |
|---|---|
| Polyolprepolymer-2 | 10.00 |
| 10% sodium hydroxide solution | qs pH 5.5 ± 0.5 |
| Purified water | qs 100 |

Example 5

Chemical Stability of the Formulation According to Example 2

| T zero | T 1 month | T 2 months | T 3 months | T 6 months |
|---|---|---|---|---|
| 0.9999 mg/g ±0.3% (100.0%) | 1.008 mg/g ±0.3% (100.8%) | 0.9913 mg/g ±0.5% (99.1%) | 0.9852 mg/g ±0.6% (98.5%) | 1.000 mg/g ±0% (100.0%) |

The chemical stability of the gel formulation described in Example 2 is measured by HPLC over 6 months at room temperature (RT). The results show that this composition is chemically stable for 6 months at room temperature.

Example 6

Chemical Stability of the Formulation According to Example 3

| T zero | T 1 month | T 2 months | T 3 months | T 6 months |
|---|---|---|---|---|
| 1.0052 mg/g ±0.3% (100.5%) | 1.008 mg/g ±0.7% (100.8%) | 0.9972 mg/g ±0.2% (99.7%) | 0.9863 mg/g ±0.1% (98.6%) | 0.9872 mg/g ±0.6% (98.7%) |

The chemical stability of the gel formulation described in Example 3 is measured by HPLC over 6 months at room temperature (RT). The results show that this composition is chemically stable for 6 months at room temperature, and at constant pH.

Moreover, the pH of the compositions was measured and shows good stability.

Example 7

General Process for Preparing an Oil-in-Water Emulsion Formulation of Cream-Gel, Cream or Lotion Type According to the Invention The process is carried out in 4 steps:

Step 1: Preparation of the Aqueous Active Phase:

Purified water, the active principle (adapalene), the hydrophilic emulsifiers such as Arlacel 165FL and Tween 80, the emollients such as glycerol and propylene glycol, the wetting agents such as Synperonic PE/L44, the chelating agent such as EDTA and the gelling agent(s) such as Carbopol, Pemulen TR1, Xantural, Methocel or Simulgel 600 are introduced with stirring using a deflocculator into a beaker that will serve as receiver for the finished product. The mixture is stirred without heating until fully dispersed. When the mixture is homogeneous, the aqueous phase is brought to 60° C. on a water bath and the methyl paraben is introduced.

Step 2: Preparation of the Fatty Phase:

The lypophilic emulsifiers such as Glucate SS/Glucamate SSE 20 or Brij 721, Tefose 1500, Eumulgin B2 PH, the oily compounds such as isostearic olepal, Cetiol SN, Crodamol DA, Speziol C18, Miglyol 812 or Cosbiol and the preservatives such as phenoxyethanol and propyl paraben are introduced with stirring using a deflocculator into an additional beaker. The mixture is adjusted to 60° C. on a water bath and, after homogenization, the volatile silicone, if present, is introduced into the composition.

Step 3: Introduction of the Polyolprepolymer:

If it is the polyolprepolymer-2, which is lipophilic, it will be introduced into the fatty phase, from the start of the weighing out. On the other hand, if it is the polyolprepolymer-15, which is hydrophilic, it will be introduced into the aqueous phase, after dispersion of the gelling agent(s).

Step 4: Emulsification:

The fatty phase is introduced gently into the aqueous phase at a temperature of 60° C. and with stirring using a deflocculator, to perform the emulsification.

Heating is maintained for 5 minutes and the hotplate is then removed to allow the product to cool gently.

The stirring is regulated as a function of the viscosity. At 40° C., the gelling-agent neutralizer (such as triethanolamine or 10% sodium hydroxide solution) is introduced, if necessary, up to a pH of 5.5±0.5. The product then has a much thicker consistency. At the end of the preparation, the pH is again checked. If it is within the norms, the sufficient quantity of water is added. The product is homogenized a final time in order to ensure good dispersion of the active principle adapalene (observation by microscope revealing a uniform dispersion free of aggregates) and the product is then packaged.

Example 8

Formulation of Cream Type Containing 0.1% Adapalene and Polyolprepolymer-2

The formula is prepared according to the procedure described in Example 7.

| Constituents | Content (% m/m) |
|---|---|
| Adapalene | 0.10 |
| Glucamate SSE 20 | 3.50 |
| Glucate SS | 3.50 |
| Propyl paraben | 0.10 |
| Phenoxyethanol | 0.50 |
| Cosbiol | 6.00 |
| Polyolprepolymer-2 | 3.00 |
| Mirasil CM5 | 13.00 |
| Na2 EDTA | 0.10 |
| Carbopol 974P NF | 0.40 |
| Glycerol | 3.00 |
| Methyl paraben | 0.10 |
| Triethanolamine | qs pH 5.5 ± 0.5 |
| Purified water | qs 100 |

Example 9

Formulation of Cream Type Containing 0.1% Adapalene and Polyolprepolymer-2

The formula is prepared according to the procedure described in Example 7.

| Constituents | Content (% m/m) |
|---|---|
| Adapalene | 0.10 |
| Glucamate SSE 20 | 3.50 |
| Glucate SS | 3.50 |
| Propyl paraben | 0.10 |
| Phenoxyethanol | 0.50 |
| Cosbiol | 6.00 |
| Polyolprepolymer-2 | 10.00 |
| Mirasil CM5 | 13.00 |
| Na2 EDTA | 0.10 |
| Carbopol 974P NF | 0.40 |
| Glycerol | 3.00 |
| Methyl paraben | 0.10 |
| Triethanolamine | qs pH 5.5 ± 0.5 |
| Purified water | qs 100 |

Example 10

Formulation of Cream Type Containing 0.1% Adapalene and Polyolprepolymer-15

The formula is prepared according to the procedure described in Example 7.

| Constituents | Content (% m/m) |
|---|---|
| Adapalene | 0.10 |
| Glucamate SSE 20 | 3.50 |
| Glucate SS | 3.50 |
| Propyl paraben | 0.10 |
| Phenoxyethanol | 0.50 |
| Cosbiol | 6.00 |
| Polyolprepolymer-15 | 3.00 |
| Mirasil CM5 | 13.00 |
| Na2 EDTA | 0.10 |
| Carbopol 974P NF | 0.40 |
| Glycerol | 3.00 |
| Methyl paraben | 0.10 |
| Triethanolamine | qs pH 5.5 ± 0.5 |
| Purified water | qs 100 |

Example 11

Formulation of Cream Type Containing 0.1% Adapalene and Polyolprepolymer-15

The formula is prepared according to the procedure described in Example 7.

| Constituents | Content (% m/m) |
|---|---|
| Adapalene | 0.10 |
| Glucamate SSE 20 | 3.50 |
| Glucate SS | 3.50 |
| Propyl paraben | 0.10 |
| Phenoxyethanol | 0.50 |
| Cosbiol | 6.00 |
| Polyolprepolymer-15 | 10.00 |
| Mirasil CM5 | 13.00 |
| Na2 EDTA | 0.10 |
| Carbopol 974P NF | 0.40 |
| Glycerol | 3.00 |
| Methyl paraben | 0.10 |
| Triethanolamine | qs pH 5.5 ± 0.5 |
| Purified water | qs 100 |

Example 12

Formulation of Lotion Type Containing 0.1% Adapalene and Polyolprepolymer-2

The formula is prepared according to the procedure described in Example 7.

| Constituents | Content (% m/m) |
|---|---|
| Adapalene | 0.10 |
| Methyl paraben | 0.15 |
| Na2 EDTA | 0.10 |
| Methocel E4M Premium | 0.10 |
| Pemulen TR1 | 0.30 |
| Isostearic olepal | 2.00 |
| Cosbiol | 8.00 |
| Polyolprepolymer-2 | 3.00 |
| Cetiol SN PH | 8.00 |
| Propyl paraben | 0.05 |
| 10 m/m % sodium hydroxide | qs pH 5.5 ± 0.5 |
| Purified water | qs 100 |

Example 13

Formulation of Lotion Type Containing 0.1% Adapalene and Polyolprepolymer-2

The formula is prepared according to the procedure described in Example 7.

| Constituents | Content (% m/m) |
|---|---|
| Adapalene | 0.10 |
| Methyl paraben | 0.15 |
| Na2 EDTA | 0.10 |
| Methocel E4M Premium | 0.10 |
| Pemulen TR1 | 0.30 |
| Isostearic olepal | 2.00 |
| Cosbiol | 8.00 |
| Polyolprepolymer-2 | 5.00 |
| Cetiol SN PH | 8.00 |
| Propyl paraben | 0.05 |
| 10 m/m % sodium hydroxide | qs pH 5.5 ± 0.5 |
| Purified water | qs 100 |

Example 14

Formulation of Lotion Type Containing 0.1% Adapalene and Polyolprepolymer-2

The formula is prepared according to the procedure described in Example 7.

| Constituents | Content (% m/m) |
|---|---|
| Adapalene | 0.10 |
| Methyl paraben | 0.15 |
| Na2 EDTA | 0.10 |
| Methocel E4M Premium | 0.10 |
| Pemulen TR1 | 0.30 |
| Isostearic olepal | 2.00 |
| Cosbiol | 8.00 |
| Polyolprepolymer-2 | 7.00 |
| Cetiol SN PH | 8.00 |
| Propyl paraben | 0.05 |

Example 15

Formulation of Lotion Type Containing 0.1% Adapalene and Polyolprepolymer-2

The formula is prepared according to the procedure described in Example 7.

| Constituents | Content (% m/m) |
| --- | --- |
| Adapalene | 0.10 |
| Methyl paraben | 0.15 |
| Simulgel 600 PHA | 1.00 |
| Brij 721 | 3.00 |
| Arlacel 165FL | 3.00 |
| Na2 EDTA | 0.10 |
| Propyl paraben | 0.05 |
| Polyolprepolymer-2 | 3.00 |
| Cosbiol | 5.00 |
| Cetiol SN PH | 5.00 |
| 10 m/m % sodium hydroxide | qs pH 5.5 ± 0.5 |
| Purified water | qs 100 |

Example 16

Formulation of Lotion Type Containing 0.1% Adapalene and Polyolprepolymer-2

The formula is prepared according to the procedure described in Example 7.

| Constituents | Content (% m/m) |
| --- | --- |
| Adapalene | 0.10 |
| Methyl paraben | 0.15 |
| Simulgel 600 PHA | 1.00 |
| Brij 721 | 3.00 |
| Arlacel 165FL | 3.00 |
| Na2 EDTA | 0.10 |
| Propyl paraben | 0.05 |
| Polyolprepolymer-2 | 5.00 |
| Cosbiol | 5.00 |
| Cetiol SN PH | 5.00 |
| 10 m/m % sodium hydroxide | qs pH 5.5 ± 0.5 |
| Purified water | qs 100 |

Example 17

Formulation of Lotion Type Containing 0.1% Adapalene and Polyolprepolymer-2

The formula is prepared according to the procedure described in Example 7.

| Constituents | Content (% m/m) |
| --- | --- |
| Adapalene | 0.10 |
| Methyl paraben | 0.15 |
| Simulgel 600 PHA | 1.00 |
| Brij 721 | 3.00 |
| Arlacel 165FL | 3.00 |
| Na2 EDTA | 0.10 |
| Propyl paraben | 0.05 |
| Polyolprepolymer-2 | 7.00 |
| Cosbiol | 5.00 |
| Cetiol SN PH | 5.00 |
| 10 m/m % sodium hydroxide | qs pH 5.5 ± 0.5 |
| Purified water | qs 100 |

Example 18

Formulation of Lotion Type Containing 0.3% Adapalene and Polyolprepolymer-2

The formula is prepared according to the procedure described in Example 7.

| Constituents | Content (% m/m) |
| --- | --- |
| Adapalene | 0.30 |
| Glycerol | 7.00 |
| Methyl paraben | 0.20 |
| Na2 EDTA | 0.10 |
| Carbopol 981NF | 0.15 |
| Propyl paraben | 0.10 |
| Eumulgin B2 PH | 3.00 |
| Arlacel 165FL | 3.00 |
| Speziol C18 Pharma | 2.00 |
| Mygliol 812 N | 7.00 |
| Polyolprepolymer-2 | 3.00 |
| Mirasil CM5 | 6.00 |
| Synperonic PE/L44 | 0.20 |
| Propylene glycol | 4.00 |
| Simulgel 600 PHA | 0.80 |
| 10 m/m % sodium hydroxide | qs pH 5.5 ± 0.5 |
| Purified water | qs 100 |

Example 19

Formulation of Cream-Gel Type Containing 0.3% Adapalene and Polyolprepolymer-2

The formula is prepared according to the procedure described in Example 7.

| Constituents | Content (% m/m) |
| --- | --- |
| Adapalene | 0.30 |
| Na2 EDTA | 0.10 |
| Methyl paraben | 0.20 |
| Xantural 180 | 0.10 |
| Glycerol | 5.00 |
| Pemulen TR1 | 0.35 |
| Propyl paraben | 0.10 |
| Miglyol 812 | 7.00 |
| Polyolprepolymer-2 | 3.00 |
| Tween 80V Pharma | 1.00 |
| Synperonic PE/L44 | 0.20 |
| Propylene glycol | 5.00 |
| 10 m/m % sodium hydroxide | qs pH 5.5 ± 0.5 |
| Purified water | qs 100 |

Example 20

Formulation of Cream-Gel Type Containing 0.3% Adapalene and Polyolprepolymer-2

The formula is prepared according to the procedure described in Example 7.

| Constituents | Content (% m/m) |
| --- | --- |
| Adapalene | 0.30 |
| Na2 EDTA | 0.10 |
| Methyl paraben | 0.20 |
| Glycerol | 5.00 |
| Propyl paraben | 0.10 |
| Miglyol 812 | 7.00 |
| Polyolprepolymer-2 | 3.00 |
| Synperonic PE/L44 | 0.20 |
| Propylene glycol | 5.00 |
| Simulgel 600 PHA | 2.20 |
| Purified water | qs 100 |

Example 21

Formulation of Cream-Gel Type Containing 0.3% Adapalene and Polyolprepolymer-2

The formula is prepared according to the procedure described in Example 7.

| Constituents | Content (% m/m) |
| --- | --- |
| Adapalene | 0.30 |
| Na2 EDTA | 0.10 |
| Methyl paraben | 0.20 |
| Pemulen TR1 | 0.30 |
| Glycerol | 5.00 |
| Carbopol 981 NF | 0.20 |
| Propyl paraben | 0.10 |
| Miglyol 812 | 7.00 |
| Polyolprepolymer-2 | 3.00 |
| Tween 80V Pharma | 1.00 |
| Propylene glycol | 5.00 |
| Synperonic PE/L44 | 0.20 |
| 10 m/m % sodium hydroxide | qs pH 5.5 ± 0.5 |
| Purified water | qs 100 |

Example 22

Formulation of Lotion Type Containing 0.1% Adapalene and 3% PP-2

The formula is prepared according to the procedure described in Example 7.

| Constituents | Content (% m/m) |
| --- | --- |
| Titriplex III | 0.1 |
| Nipagin M | 0.2 |
| Carbopol 981 | 0.2 |
| Phenoxetol | 1.0 |
| Nipasol M | 0.1 |
| Speziol C18 Pharma | 2.0 |
| Tefose 1500 | 5.0 |
| Miglyol 812N | 7.0 |
| Polyolprepolymer-2 | 3.0 |
| Adapalene | 0.1 |
| Synperonic PE/L44 | 0.2 |
| Propylene glycol USP/EP | 4.0 |
| 10 m/m % sodium hydroxide | qs pH 5.5 ± 0.5 |
| Purified water | qs 100 |

Example 23

Formulation of Lotion Type Containing 0.3% Adapalene and 3% PP-2

The formula is prepared according to the procedure described in Example 7.

| Constituents | Content (% m/m) |
| --- | --- |
| Titriplex III | 0.1 |
| Nipagin M | 0.2 |
| Carbopol 981 | 0.2 |
| Phenoxetol | 1.0 |
| Nipasol M | 0.1 |
| Speziol C18 Pharma | 2.0 |
| Tefose 1500 | 5.0 |
| Miglyol 812N | 7.0 |
| Polyolprepolymer-2 | 3.0 |
| Adapalene | 0.3 |
| Synperonic PE/L44 | 0.2 |
| Propylene glycol USP/EP | 4.0 |
| 10 m/m % sodium hydroxide | qs pH 5.5 ± 0.5 |
| Purified water | qs 100 |

Specifications at Time Zero:

| | |
| --- | --- |
| Macroscopic appearance | Very fluid glossy white milk |
| pH at T = 24 hours | 5.4 |
| Microscopic appearance | globules ≤ 2.5 to 12.5 μm... Adapalene well distributed as 10 to 25 μm lumps. |
| Viscosity: τ (4s-1) flow threshold in Pa·s$^{-1}$ | 12 |
| Analytical assay at T0 | 99.6% |

The physical and chemical stabilities of this composition were measured. The results are given below:

| | | T1 month | T2 months | T3 months |
| --- | --- | --- | --- | --- |
| RT | Viscosity: τ (4s-1) flow threshold in Pa·s$^{-1}$ | 13 | 12 | 12 |
| | Macroscopic appearance | Compliance | Compliance | Compliance/ |
| | pH | 5.4 | 5.4 | |
| | Microscopic appearance | Compliance | Compliance | Compliance |
| | Analytical assay | 99.7% | 98.6% | 98.8% |
| 4° C. | Macroscopic appearance | Compliance | Compliance | Compliance |
| | Microscopic appearance | Compliance | Compliance | Compliance |
| 40° C. | Macroscopic appearance | Compliance | Compliance | Compliance |

|  | T1 month | T2 months | T3 months |
|---|---|---|---|
| Microscopic appearance | Compliance | Compliance | Compliance |
| Analytical assay | 98.9% | 96.5% | 98.7% |

The composition is thus chemically and physically stable.

Example 24

Formulation of the Lotion Type Cream-Gel Containing 0.3% Adapalene and 3% PP-2

The formula is prepared according to the procedure described in Example 7.

| Composition | Content (% m/m) |
|---|---|
| Titriplex III | 0.1 |
| Nipagin M | 0.2 |
| Glycerol | 7.0 |
| Carbopol 981 NF | 0.15 |
| Benzalkonium chloride | 0.05 |
| Nipasol M | 0.1 |
| Eumulgin B2 PH | 3.0 |
| Speziol C18 Pharma | 2.0 |
| Miglyol 812 N | 7.0 |
| Polyolprepolymer-2 | 3.0 |
| Arlacel 165 FL | 3.0 |
| Mirasil CM5 | 6.0 |
| Synperonic PE/L44 | 0.2 |
| Propylene glycol USP/EP | 4.0 |
| Adapalene | 0.3 |
| Simulgel 600 | 0.8 |
| 10 m/m % sodium hydroxide | qs pH 5.5 ± 0.5 |
| Purified water | qs 100 |

Specifications at Time Zero:

| Macroscopic appearance | Glossy thick white milk |
|---|---|
| pH at T24 hours | 5.7 |
| Microscopic appearance | Globules ≤ 2.5 μ and up to 10 μ Adapalene well dispersed as lumps ≤ 2.5 μm to 10 μm |
| Viscosity: τ (4s-1) in Pa · s$^{-1}$ | 44 |
| Analytical assay at T0 | 98.2% |

The physical and chemical stabilities of this composition were measured. The results are given below:

|  |  | T1 month | T2 months |
|---|---|---|---|
| RT | Viscosity: τ (4s-1) flow threshold in Pa · s$^{-1}$ | 42 | NR |
|  | Macroscopic appearance | Compliance | Compliance |
|  | pH | 5.76 | NR |
|  | Microscopic appearance | Compliance | Compliance |
|  | Analytical assay | 98.2% | 98.3 |
| 4° C. | Macroscopic appearance | Compliance | Compliance |
|  | Microscopic appearance | Compliance | Compliance |

|  |  | T1 month | T2 months |
|---|---|---|---|
| 40° C. | Macroscopic appearance | Compliance | Compliance |
|  | Microscopic appearance | Compliance | Compliance |
|  | Analytical assay | 98.3% | 104.8 |

The composition is thus physically and chemically stable.

Example 25

Formulation of the Type Lotion Containing 0.3% Adapalene and 3% PP-2

The formula is prepared according to the procedure described in Example 7.

| Composition | Content (% m/m) |
|---|---|
| Titriplex III | 0.1 |
| Nipagin M | 0.2 |
| Carbopol 980 NF | 0.15 |
| Carbopol 981 NF | 0.3 |
| Glycerol | 3.0 |
| Phenoxetol | 1.0 |
| Nipasol M | 0.2 |
| Glucate SS | 1.0 |
| Glucamate SSE20 | 5.0 |
| Miglyol 812 N | 6.0 |
| Polyolprepolymer-2 | 3.0 |
| Q7-9120 silicone fluid 20 cSt | 1.0 |
| Synperonic PE/L44 | 0.2 |
| Propylene glycol USP/EP | 4 |
| Adapalene | 0.3 |
| 10 m/m % sodium hydroxide | qs pH 5, 5 ± 0.5 |
| Purified water | qs 100 |

Specifications at Time Zero:

| Macroscopic appearance | Glossy white milk |
|---|---|
| pH at T = 24 hours | 5.4 |
| Microscopic appearance | globules ≤ 2.5 μm Adapalene distributed in globules from 2.5 to 20 μm. |
| Viscosity: τ (4s-1) in Pa · s$^{-1}$ | 37 |
| Analytical assay at T0 | 102.0% |

The physical and chemical stabilities of this composition were measured. The results are given below:

|  |  | T1 month | T2 months | T3 months |
|---|---|---|---|---|
| RT | Viscosity: τ (4s-1) in Pa · s$^{-1}$ | 40 | 42 | NR |
|  | Macroscopic appearance | Compliance | Compliance | Compliance |
|  | pH | 5.4 | 5.4 | 5.4 |
|  | Microscopic appearance | Compliance | Compliance | Compliance |
|  | Analytical assay | 101.4% | 102.0 | 102.7 |
| 4° C. | Macroscopic appearance | Compliance | Compliance | Compliance |

|  |  | T1 month | T2 months | T3 months |
|---|---|---|---|---|
| 40° C. | Microscopic appearance | Compliance | Compliance | Compliance |
|  | Macroscopic appearance | Compliance | Compliance | Compliance |
|  | Microscopic appearance | Compliance | Compliance | Compliance |
|  | Analytical assay | 102.8% | 102.0 | 104.8 |

The composition is thus chemically and physically stable.

Example 26

Formulation of the Type Cream-Gel Containing 0.3% Adapalene and 3% PP-2

The formula is prepared according to the procedure described in Example 7.

| Composition | Content (% m/m) |
|---|---|
| Titriplex III | 0.1 |
| Nipagin M | 0.2– |
| Propylene glycol | 3.0 |
| Glycerol | 5.0 |
| Nipabutyl | 0.2 |
| Nipasol M | 0.1 |
| Miglyol 812 N | 7.0 |
| Polyolprepolymer-2 | 3.0 |
| Benzyl alcohol | 1.0 |
| Synperonic PE/L44 | 0.2 |
| Propylene glycol USP/EP | 4.0 |
| Simulgel 600 PHA | 2.0 |
| Adapalene | 0.3 |
| Purified water | qs 100 |

Specifications at Time Zero:

| | |
|---|---|
| Macroscopic appearance | Quite fluid glossy white milk |
| pH at T = 24 hours | 5.2 |
| Microscopic appearance | Globules ≤ 2.5 μm to 12.5 μm. Adapalene distributed in globules from 2.5 to 20 μm. |
| Viscosity: τ (4s-1) flow threshold in Pa · s$^{-1}$ | 18 |
| Analytical assay at T0 | 98.7 |

The physical and chemical stabilities of this composition were measured. The results are given below:

|  |  | T1 month | T2 months |
|---|---|---|---|
| RT | Viscosity: τ (4s-1) in Pa · s$^{-1}$ | NR | NR |
|  | Macroscopic appearance | Compliance | Compliance |
|  | pH |  |  |
|  | Microscopic appearance | Compliance | Compliance |
|  | Analytical assay | 98.5% | 98.6 |
| 4° C. | Macroscopic appearance | Compliance | Compliance |
|  | Microscopic appearance | Compliance | Compliance |
| 40° C. | Macroscopic appearance | Compliance | Compliance |
|  | Microscopic appearance | Compliance | Compliance |
|  | Analytical assay | 98.8% | 101.7% |

The composition is thus physically and chemically stable.

Example 27

Formulation of the Type Lotion Containing 0.3% Adapalene and 3% PP-2

The formula is prepared according to the procedure described in Example 7.

| Composition | Content (% m/m) |
|---|---|
| Titriplex III | 0.1 |
| Pemulen TR1 NF | 0.3 |
| Glycerol | 5.0 |
| Carbopol 981 NF | 0.2 |
| Nipasol M | 0.2 |
| Nipabutyl | 0.2 |
| Miglyol 812 N | 7.0 |
| Benzyl alcohol | 1 |
| Polyolprepolymer-2 | 3.0 |
| Synperonic PE/L44 | 0.2 |
| Tween 80 V Pharma | 1.0 |
| Propylene glycol USP/EP | 7.0 |
| Adapalene | 0.3 |
| 10 m/m % sodium hydroxide | qs pH 5, 5 ± 0.5 |
| Purified water | qs 100 |

Specifications at Time Zero:

| | |
|---|---|
| Macroscopic appearance | Gelled glossy white milk |
| pH at T = 24 hours | 5.6 |
| Microscopic appearance | Globules ≤ 2.5 μm to 7.5 μm. Adapalene in globules of 2.5 to 12.5 μm. |
| Viscosity: τ (4s-1) in Pa · s$^{-1}$ | 34 |
| Analytical assay at T0 | 99.4 |

The physical and chemical stabilities of this composition were measured. The results are given below:

|  |  | T1 month | T2 months | T3 months |
|---|---|---|---|---|
| RT | Viscosity: τ (4s-1) in Pa · s$^{-1}$ | 38 | 35 | 36 |
|  | Macroscopic appearance | Compliance | Compliance | Compliance |
|  | pH | 5.7 | 5.6 | 5.6 |
|  | Microscopic appearance | Compliance | Compliance | Compliance |
|  | Analytical assay | 99.7 | 99.2 | 100.2 |
| 4° C. | Macroscopic appearance | Compliance | Compliance | Compliance |
|  | Microscopic appearance | Compliance | Compliance | Compliance |
| 40° C. | Macroscopic appearance | Compliance | Compliance | Compliance |

-continued

|  | T1 month | T2 months | T3 months |
|---|---|---|---|
| Microscopic appearance | Compliance | Compliance | Compliance |
| Analytical assay | 99.5 | 106.2 | 100.3 |

The composition is thus physically and chemically stable.

Example 28

Study of In Vitro Release-Penetration

The present study is for comparing in vitro the release-penetration into human skin without occlusion of adapalene formulated at 0.1% (m/m) in a gel containing 1% PP-2 (formulation according to Example 2), formulated at 0.1% (m/m) in a gel containing 3% PP-2 (formulation according to Example 3) and in a reference gel containing 0.1% adapalene.

The absorption studies were performed using excised human skin mounted under static conditions for a period of 16 hours. Three samples of skin obtained from women (68 years old) were used. An amount of 10 mg of each formula (10 µg of adapalene) was applied to a 1 cm² area of skin. The adapalene concentrations in the fluid fractions collected over time and remaining in the skin at the end of the study were evaluated by the HPLC method with fluorescence detection (based on a validated method. Quantification limit: 1 ng·mL$^{-1}$).

The experimental results are reported in the table below:

|  | Reference gel containing 0.1% adapalene | Formulation according to Example 2 | Formulation according to Example 3 |
|---|---|---|---|
| Dose absorbed in epidermis + stratum corneum | 0.11 µg | 0.10 µg | 0.21 µg |
| Dose absorbed in dermis | 0.013 µg | 0.003 µg | 0.009 µg |
| Epidermis/dermis ratio | 9 | 33 | 23 |

These results show that, irrespective of the formula tested, the adapalene is mainly distributed in the epidermis (stratum corneum included) and to a lesser extent in the dermis. The epidermis/dermis ratios for the formulations according to Examples 2 and 3 are markedly higher than the epidermis/dermis ratio for the reference gel containing 0.1% adapalene. These results suggest that the presence of PP-2 in the formulations according to the invention considerably modifies the distribution of adapalene in the skin by retaining the adapalene mainly in the stratum corneum and epidermis upper layers. This example thus demonstrates the "reservoir effect" of the formulations according to the invention.

Example 29

Tolerance Study in BALB/c Mice

The present study is for comparing the irritant power of a reference gel containing 0.1% adapalene with that of three 0.1% adapalene formulations in gel form containing a polyurethane polymer at various concentrations, and also placebos thereof, on the skin of the ear of the BALB/c mouse after repeated topical applications for 6 days.

The daily topical application (20 µl) of the test products is performed on the inner face of the ear of BALB/c mice divided into ten groups (female mice about 8 weeks old) at a rate of one application per day for 6 days. The test products are:
Group 1: acetone (control vehicle)
Group 2: placebo reference gel (control vehicle)
Group 3: placebo formulation (without 0.1% adapalene) of Example 2 (1% PP-2) (control vehicle)
Group 4: placebo formulation (without 0.1% adapalene) of Example 3 (3% PP-2) (control vehicle)
Group 5: placebo formulation (without 0.1% adapalene) of Example 4 (10% PP-2) (control vehicle)
Group 6: reference gel containing 0.1% adapalene
Group 7: formulation of Example 2 (1% PP-2)
Group 8: formulation of Example 3 (3% PP-2)
Group 9: placebo formulation of Example 4 (10% PP-2)
Group 10: acetone+0.1% (m/m) adapalene The evaluation is performed by measuring the thickness of the ear by means of the Oditest and by clinical observation of the animals from the $2^{nd}$ to the $19^{th}$ day.

The results are reported in the table below and in FIGS. 1 to 4, in which:

FIG. 1 shows the kinetics of the mean thickness of the mouse ears from the $2^{nd}$ and $19^{th}$ days for the various test products with:
acetone (curve (1A))
placebo reference gel (curve (1B))
placebo Ex. 2 (1% PP-2) (curve (1C))
placebo Ex. 3 (3% PP-2) (curve (1D))
placebo Ex. 4 (10% PP-2) (curve (1E))

These placebo kinetics show that the various placebo formulations used are not irritant and behave like acetone.

Figure 2:
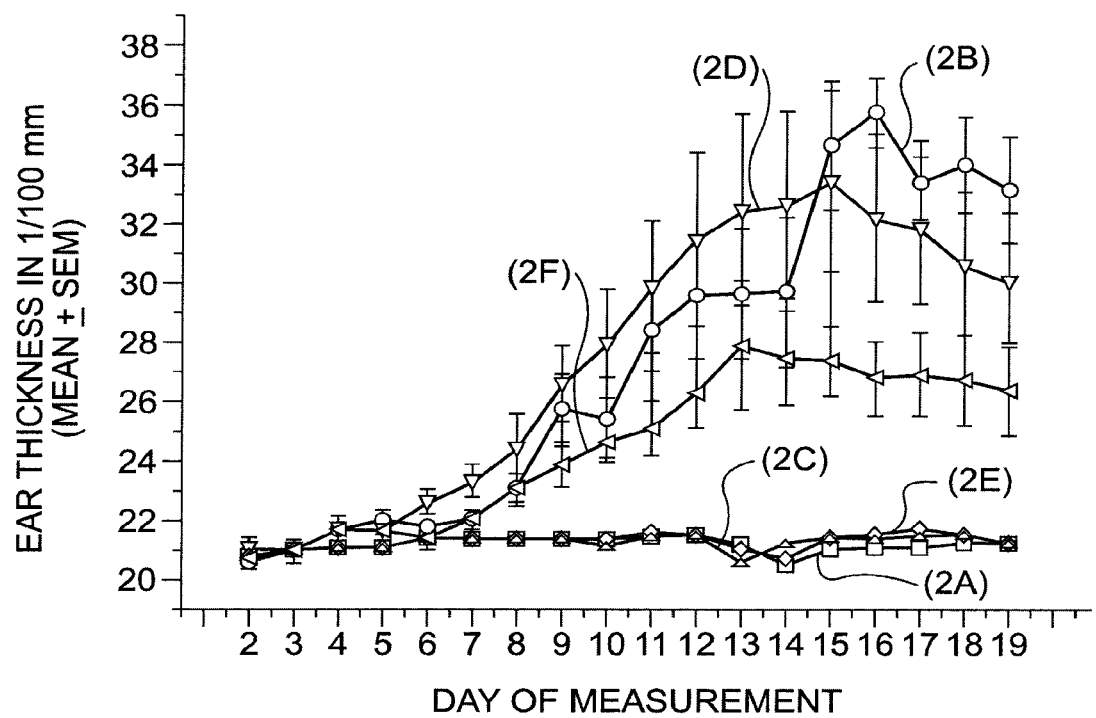

FIG. 2 shows the kinetics of the mean thickness of the mouse ears from the $2^{nd}$ and $19^{th}$ days for the various test products with:
acetone (curve (2A))
acetone+0.1% adapalene (curve (2B))
placebo reference gel (curve (2C))
reference gel containing 0.1% adapalene (curve (2D))
placebo Example 2 (1% PP-2) (curve (2E))
Example 2 (1% PP-2) (curve (2F))

These kinetics show that the reference gel containing 0.1% adapalene is irritant from the sixth day with a 31% increase in the area under the curve relative to its placebo (placebo reference gel). Similarly, the product acetone+0.1% adapalene is also irritant and shows a 30% increase in the area under the curve relative to its placebo (acetone). Surprisingly, the formulation according to Example 2 (1% PP-2) is only half as irritant as the reference gel containing 0.1% adapalene and shows an increase in the area under the curve of only 15% relative to its placebo (placebo Example 2 (1% PP-2)).

Figure 3:
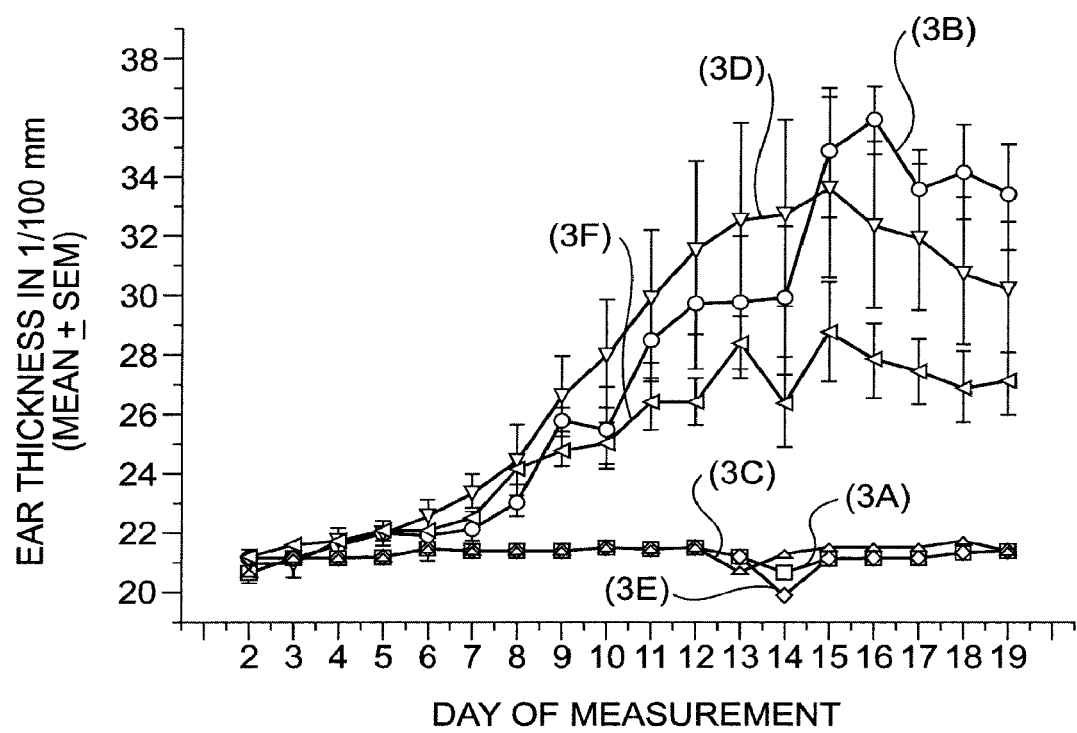

FIG. 3 shows the kinetics of the mean thickness of the mouse ears from the $2^{nd}$ and $19^{th}$ days for the various test products with:
acetone (curve (3A))
acetone+0.1% adapalene (curve (3B))
placebo reference gel (curve (3C))
reference gel containing 0.1% adapalene (curve (3D))
placebo Example 3 (3% PP-2) (curve (3E))
Example 3 (3% PP-2) (curve (3F))

These kinetics also show, surprisingly, that the formulation according to Example 3 is less irritant than the reference gel containing 0.1% adapalene. This formulation according to Example 3 (3% PP-2) also shows an increase in the area under the curve of only 19% relative to its placebo (placebo Example 3 (3% PP-2)).

Figure 4:
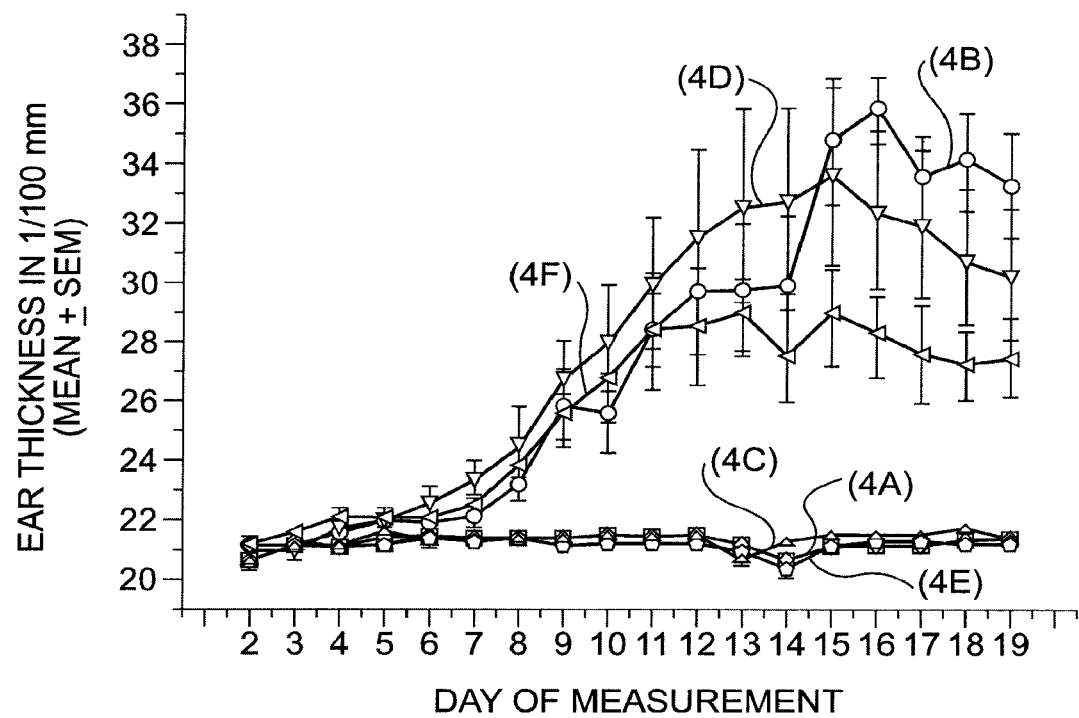

FIG. 4 shows the kinetics of the mean thickness of the mouse ears from the $2^{nd}$ and $19^{th}$ days for the various test products with:
- acetone (curve (4A))
- acetone+0.1% adapalene (curve (4B))
- placebo reference gel (curve (4C))
- reference gel containing 0.1% adapalene (curve (4D))
- placebo Example 4 (10% PP-2) (curve (4E))
- Example 4 (10% PP-2) (curve (4F))

These kinetics show that the formulation according to Example 4 is less irritant than the reference gel containing 0.1% adapalene. This formulation according to Example 3 (3% PP-2) similarly shows an increase in the area under the curve of 22% relative to its placebo (placebo Example 4 (3% PP-2)).

When a comparison is made of the kinetics of the various formulations described, respectively, in Examples 2 to 4, it is seen that these three formulations have very similar kinetics. It is impossible to differentiate them. Surprisingly, these three formulations are all less irritant than the reference gel containing 0.1% adapalene and than 0.1% (m/m) adapalene in acetone.

Summary table of the results of the areas under the curve (AUC) for the ear thickness kinetics.

|  | AUC D2-D19 | | |
| --- | --- | --- | --- |
|  | Mean | Standard error of mean (SEM) | Increase in AUC versus placebo (%) |
| Group 2 (placebo reference gel) | 383.3 | 2.1 | — |
| Group 3 (placebo Example 2) | 385.8 | 3.1 | — |
| Group 4 (placebo Example 3) | 380.7 | 2.2 | — |
| Group 5 (placebo Example 4) | 379.5 | 2.6 | — |
| Group 6 (reference gel containing 0.1% adapalene) | 502.0 | 30.2 | 31.0 |
| Group 7 (Example 2) | 445.4 | 15.0 | 15.4 |
| Group 8 (Example 3) | 453.6 | 11.7 | 19.2 |
| Group 9 (Example 4) | 461.8 | 17.1 | 21.7 |

The results of the study show that, after repeated topical applications of 20 µl of test product from D1 to D6 to the BALB/c mouse ear:

the test placebos (respectively, "placebo reference gel", "placebo Example 2", "placebo Example 3" and "placebo Example 4") are not irritant and show fully superposable kinetics;

the test formulations described in Examples 2, 3 and 4 increase the thickness of the ear by 15%, 19% to 22%, respectively, relative to their placebos. They are all less irritant than the "reference gel containing 0.1% adapalene" and difficult to differentiate from each other.

This example demonstrates that the formulae according to the invention show better in vivo tolerance than the "reference gel containing 0.1% adapalene".

The table below compares the various formulations containing 0.1% adapalene with the untreated placebo so as to demonstrate the effect of the polyurethane polymer on the tolerance.

|  | AUC D2-D19 | | Increase in AUS versus untreated (%) | Comparison reference gel containing 0.1% adapalene/ test formula |
| --- | --- | --- | --- | --- |
|  | Mean | Standard error of mean (SEM) | | |
| Group 2 (placebo reference gel) | 383.3 | 2.1 | — | — |
| Group 3 (placebo Example 2) | 385.8 | 3.1 | — | — |
| Group 4 (placebo Example 3) | 380.7 | 2.2 | — | — |
| Group 5 (placebo Example 4) | 379.5 | 2.6 | — | — |
| Group 6 (reference gel containing 0.1% adapalene) | 502.0 | 30.2 | 31.2 | 1.0 |
| Group 7 (Example 2) | 445.4 | 15.0 | 16.4 | 1.9 |
| Group 8 (Example 3) | 453.6 | 11.7 | 18.6 | 1.7 |
| Group 9 (Example 4) | 461.8 | 17.1 | 17.2 | 1.8 |

Thus, irrespective of the content of polyurethane polymer 1: 3% or 10%, the formulations are tolerated 2 times better than in the absence of polyurethane polymers.

Example 30

Study of the Comedolytic Activity on Rhino Mice

The present study is aimed at evaluating the comedolytic activity of the reference gel containing 0.1% adapalene and of two 0.1% adapalene formulations in gel form with a polyurethane polymer at different concentrations, and also their placebos, on the skin of the back of RHINO FVB/N RJ-hr$^{rh}$ mice (Rhino) after repeated topical applications for 18 days.

The daily topical application (50 µl) of the test products is performed on the skin of the back of Rhino mice divided into seven groups (approximately 7-week-old mice) at a rate of one application per day for 18 days. The test products are:
- Group 1: acetone (control vehicle)
- Group 2: placebo formulation (without 0.1% adapalene) of Example 3 (3% PP-2) (control vehicle)
- Group 3: acetone+0.01% (m/m) 2-(5,5,8,8-tetramethyl-5,6,7,8-tetrahydronaphthalen-2-yl)benzo[b]thiophene-6-carboxylic acid (positive control)
- Group 4: acetone+0.1% (m/m) adapalene
- Group 5: reference gel containing 0.1% adapalene
- Group 6: formulation of Example 2 (1% PP-2)
- Group 7: formulation of Example 3 (3% PP-2)

The tolerance evaluation is made by clinical observation of the dorsal epidermis with the following observation parameters: oedema, erythema and squamae 3 times a week for 19 days.

The comedolytic activity is evaluated by measuring the transepidermal water loss (TWL) on days D4, D11 and D19, by measuring the thickness of the epidermis, by counting the number of comedones/cm and by weighing the animals on days D1, D4, D11 and D19.

Figure 5:
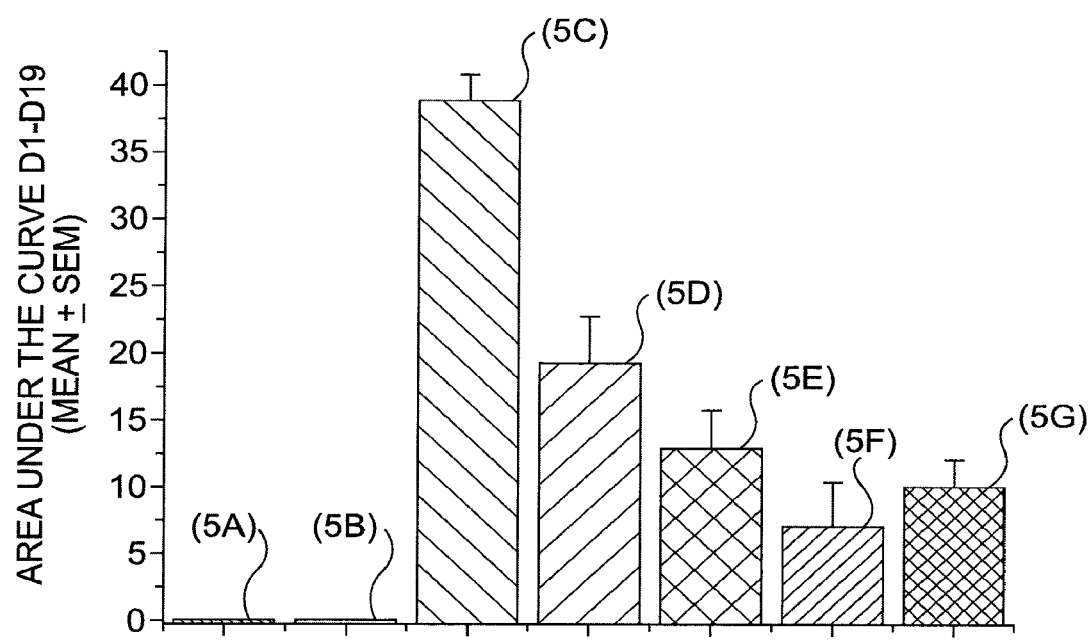
FIGS. 5 to 8 show the results of a study for evaluating the comedolytic activity of a reference gel containing 0.1% adapalene and of two 0.1% adapalene formulations in gel form with a polyurethane polymer at various concentrations, and also placebos thereof, on dorsal skin of RHINO FVB/N RJ-hr$^{rh}$ mice (Rhino) after repeated topical applications for 18 days.

FIG. 5 shows the results of the areas under the curve for the tolerance evaluation from the $1^{st}$ and $19^{th}$ day for the various test products with:

acetone (control vehicle) (curve (5A))
formulation of Example 3 (3% PP-2) without 0.1% adapalene (control vehicle) (curve (5B))
acetone+0.01% (m/m) 2-(5,5,8,8-tetramethyl-5,6,7,8-tetrahydronaphthalen-2-yl)benzo[b]thiophene-6-carboxylic acid (positive control) (curve (5C))
acetone+0.1% (m/m) adapalene (curve 5D))
reference gel containing 0.1% adapalene (curve (5E))
formulation of Example 2 (1% PP-2) (curve (5F))
formulation of Example 3 (3% PP-2) (curve (5G))

The results of this study show that the formulations according to Examples 2 and 3 are less irritant than the reference gel containing 0.1% adapalene. These formulations according to Examples 2 (1% PP-2) and 3 (3% PP-2) effectively show a reduction in the area under the curve of 45% to 22%, respectively, relative to the reference gel containing 0.1% adapalene.

Figure 6:
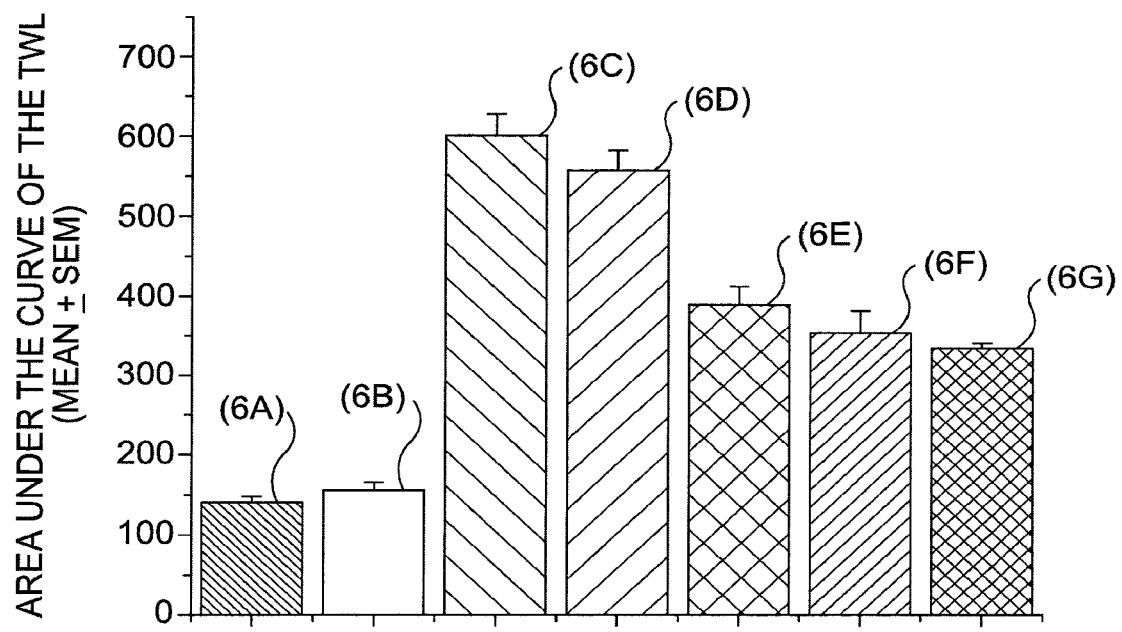

FIG. 6 shows the results of the areas under the curve (AUC) for the transepidermal water loss (TWL) after 18 days of topical treatment for the various test products with:
acetone (control vehicle) (curve (6A))
formulation of Example 3 (3% PP-2) without 0.1% adapalene (control vehicle) (curve (6B))
acetone+0.01% (m/m) 2-(5,5,8,8-tetramethyl-5,6,7,8-tetrahydronaphthalen-2-yl)benzo[b]thiophene-6-carboxylic acid (positive control) (curve (6C))
acetone+0.1% (m/m) adapalene (curve (6D))
reference gel containing 0.1% adapalene (curve (6E))
formulation of Example 2 (1% PP-2) (curve (6F))
formulation of Example 3 (3% PP-2) (curve (6G))

The TWL quantifies the impairment in the skin barrier by measuring the gradient of water vapor that is established in a layer 10 mm thick above the surface of the skin.

The results of this study show that the formulations of Examples 2 and 3 according to the invention increase the TWL by 129% to 118%, respectively. These values are markedly lower than the TWL increases observed for the acetone+0.01% (m/m) 2-(5,5,8,8-tetramethyl-5,6,7,8-tetrahydronaphthalen-2-yl)benzo[b]thiophene-6-carboxylic acid (332%) and acetone+0.1% (m/m) adapalene (299%) formulations and less than the TWL increase observed for the reference gel formulation containing 0.1% adapalene (152%). FIG. 6 thus shows that the formulations according to the invention afford better protection of the skin barrier than the reference gel containing 0.1% adapalene.

Figure 7:
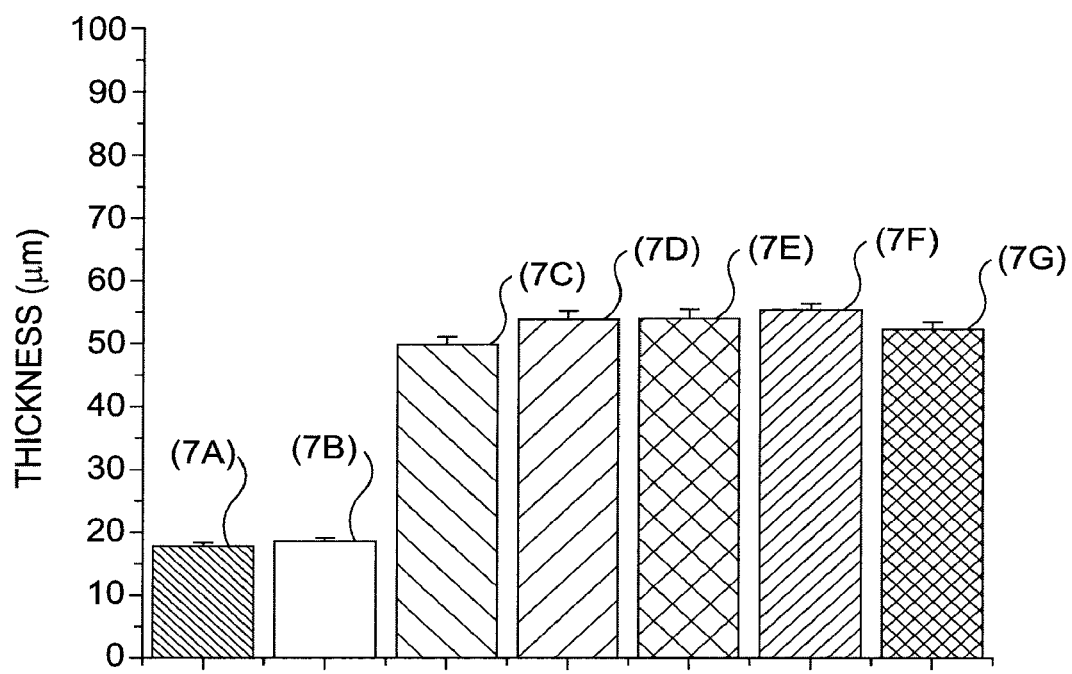

FIG. 7 shows the results of the measurement of the thickness of the epidermis after 18 days of topical treatment for the various test products with:
acetone (control vehicle) (curve (7A))
formulation of Example 3 (3% PP-2) without 0.1% adapalene (control vehicle) (curve (7B))
acetone+0.01% (m/m) 2-(5,5,8,8-tetramethyl-5,6,7,8-tetrahydronaphthalen-2-yl)benzo[b]thiophene-6-carboxylic acid (positive control) (curve (7C))
acetone+0.1% (m/m) adapalene (curve 7D))
reference gel containing 0.1% adapalene (curve (7E))
formulation of Example 2 (1% PP-2) (curve (7F))
formulation of Example 3 (3% PP-2) (curve (7G))

The results of this study show that an equivalent increase in the thickness of the epidermis is observed for all the formulations containing adapalene.

Figure 8:
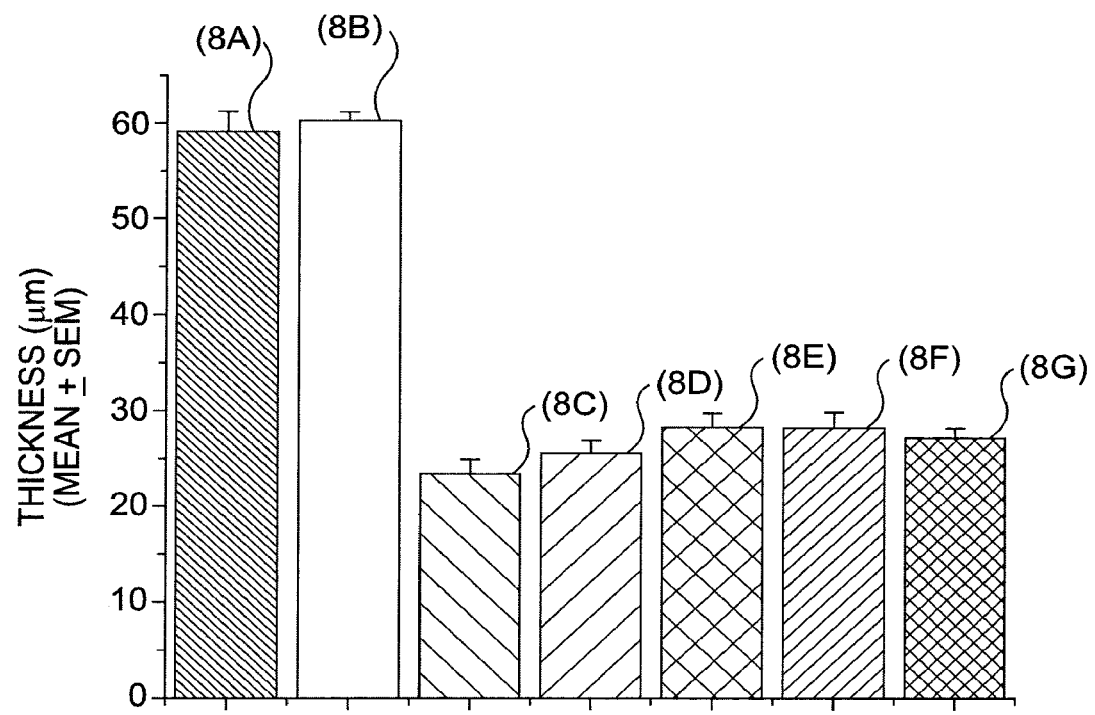

FIG. 8 shows the results of the counting of the number of comedones per centimeter (cm) on the back of Rhino mice after 18 days of topical treatment for the various test products with:
acetone (control vehicle) (curve (8A))
formulation of Example 3 (3% PP-2) without 0.1% adapalene (control vehicle) (curve (8B))
acetone+0.01% (m/m) 2-(5,5,8,8-tetramethyl-5,6,7,8-tetrahydronaphthalen-2-yl)benzo[b]thiophene-6-carboxylic acid (positive control) (curve (8C))
acetone+0.1% (m/m) adapalene (curve 8D))
reference gel containing 0.1% adapalene (curve (8E))
formulation of Example 2 (1% PP-2) (curve (8F))
formulation of Example 3 (3% PP-2) (curve (8G))

The results of this study show that the skins treated with the placebos (acetone or formulation of Example 3 (3% PP-2) without 0.1% adapalene) show a similar and high number of comedones per centimeter, of from 58 and 60. On the other hand, the skins treated with formulations containing the active principle adapalene (acetone+0.1% (m/m) adapalene, reference gel containing 0.1% adapalene, formulations of Examples 2 and 3) show a comparable and low number of comedones per centimeter, of from 25 and 27. It appears, with regard to FIG. 8, that the formulations according to the invention have comedolytic activity comparable to the reference gel containing 0.1% adapalene.

The table below shows the changes in the weight of the mice of the 7 groups of the study, from the $19^{th}$ day and the $1^{st}$ day:

| Change in weight of the Rhino mice (%) D19-D1 | | |
|---|---|---|
| | Mean | Standard error of mean (SEM) |
| Group 1: acetone (control vehicle) | 13.2 | 1.41 |
| Group 2: Example 3 without 0.1% adapalene (control vehicle) | 11.0 | 2.42 |
| Group 3: acetone + 0.01% (m/m) 2-(5,5,8,8-tetramethyl-5,6,7,8-tetrahydronaphthalen-2-yl)benzo[b]thiophene-6-carboxylic acid (positive control) | 10.4 | 5.97 |
| Group 4: acetone + 0.1% (m/m) adapalene | 9.2 | 1.54 |
| Group 5: reference gel containing 0.1% adapalene | 11.0 | 2.20 |
| Group 6: formulation of Example 2 (1% PP-2) | 8.1 | 1.70 |
| Group 7: formulation of Example 3 (3% PP-2) | 8.6 | 2.18 |

The results of this study show that after 18 days of topical treatment, the animals do not show any weight loss. Furthermore, the above table shows that there is no significant difference from the animals treated with the controls and the animals treated with the various adapalene formulations.

This example, and the studies that follow therefrom, demonstrate that the formulae according to the invention show better in vivo tolerance than the reference gel containing 0.1% adapalene, while having comedolytic activity equivalent to that of the reference gel containing 0.1% adapalene.

Example 31

Study of In Vitro Release-Penetration

The present study is for comparing in vitro the release-penetration into human skin without occlusion of adapalene formulated at 0.3% (m/m) in a lotion containing 3% PP-2 (formulation according to Example 23), formulated at 0.3%

(m/m) in a lotion containing 3% PP-2 (formulation according to Example 25) and in a reference gel containing 0.1% adapalene.

The absorption studies were performed using excised human skin mounted under static conditions for a period of 16 hours. Three samples of skin obtained from women (68 years old) were used. An amount of 30 mg of each formula (30 μg of adapalene) was applied to a 1 cm² area of skin. The adapalene concentrations in the fluid fractions collected over time and remaining in the skin at the end of the study were evaluated by the HPLC method with fluorescence detection (based on a validated method. Quantification limit: 1 ng·mL⁻¹).

The experimental results are reported in the table below:

|  | adapalene gel |
| --- | --- |
| in Stratum corneum |  |
| in Epiderme |  |
| in derme |  |
| in Epiderme + Stratum corneum + Derme |  |

These results show that in invention formula tested, the adapalene is mainly distributed in the stratum corneum. These results suggest that the presence of PP-2 in the formulations according to the invention does not interfere with the active principal penetration.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, stable cosmetic/dermatological composition which comprises at least one naphthoic acid compound useful for the treatment of keratinization disorders and an anti-irritant amount of at least one polyurethane polymer, said at least one naphthoic acid compound being dispersed in undissolved form therein, said at least one polyurethane polymer being present in an amount sufficient to decrease the irritant effect of the naphthoic acid compound dispersed in undissolved form therein, formulated into a topically applicable, physiologically acceptable medium therefor, wherein the composition is devoid of extract of saw palmetto berries.

2. The cosmetic/dermatological composition as defined by claim 1, said at least one naphthoic acid compound having the formula (I):

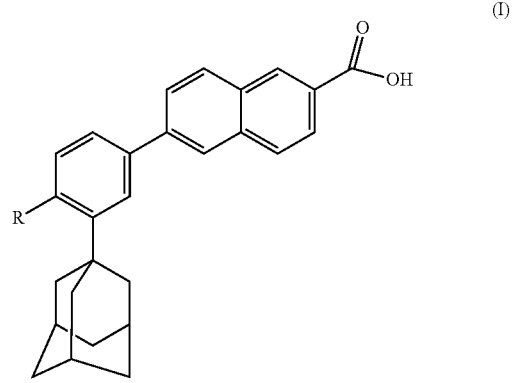

in which R is a hydrogen atom, a hydroxyl radical, a branched or unbranched alkyl radical having from 1 to 4 carbon atoms, an alkoxy radical having from 1 to 10 carbon atoms or a cycloaliphatic radical.

3. The cosmetic/dermatological composition as defined by claim 1, the concentration of said at least one naphthoic acid compound ranging from 0.001% to 10% by weight relative to the total weight of the composition.

4. The cosmetic/dermatological composition as defined by claim 1, said at least one naphthoic acid compound being selected from the group consisting of 6-[3-(1-adamantyl)-4-methoxyphenyl]-2-naphthoic acid, 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid.

5. The cosmetic/dermatological composition as defined by claim 4, said at least one naphthoic acid compound comprising 6-[3-(1-adamantyl)-4-methoxyphenyl]-2-naphthoic acid.

6. The cosmetic/dermatological composition as defined by claim 5, the concentration of said 6-[3-(1-adamantyl)-4-methoxyphenyl]-2-naphthoic acid being about 0.1% by weight relative to the total weight of the composition.

7. The cosmetic/dermatological composition as defined by claim 5, the concentration of said 6-[3-(1-adamantyl)-4-methoxyphenyl]-2-naphthoic acid being about 0.3% by weight relative to the total weight of the composition.

8. The cosmetic/dermatological composition as defined by claim 1, said at least one naphthoic acid compound comprising the only active principle therein.

9. The cosmetic/dermatological composition as defined by claim 1, said at least one polyurethane polymer being selected from the group consisting of the polyolprepolymer of type 2, the polyolprepolymer of type 14 and the polyolprepolymer of type 15, and mixture thereof.

10. The cosmetic/dermatological composition as defined by claim 9, said at least one polyurethane polymer being the polyolprepolymer of type 2.

11. The cosmetic/dermatological composition as defined by claim 1, the concentration of said at least one polyurethane polymer type ranging from 0.5% to 20% by weight relative to the total weight of the composition.

12. The cosmetic/dermatological composition as defined by claim 11, wherein the concentration of said at least one polyurethane polymer is about 1%, 3%, 7% or 10% by weight relative to the total weight thereof.

13. The cosmetic/dermatological composition as defined by claim 1, formulated as an aqueous, aqueous-alcoholic or oily dispersion, a dispersion of the lotion type, an aqueous, anhydrous or lipophilic gel, an emulsion of liquid or semi-liquid consistency of the milk type, obtained by dispersing a fatty phase in an aqueous phase or vice versa, or a suspension or emulsion of soft, semi-liquid or solid consistency of the cream, gel, cream-gel or pomade type, or as a microemulsion, microcapsules, microparticles or vesicular dispersion of ionic and/or nonionic type.

14. The cosmetic/dermatological composition as defined by claim 13, formulated as a gel.

15. The cosmetic/dermatological composition as defined by claim 13, formulated a cream.

16. The cosmetic/dermatological composition as defined by claim 13, formulated a lotion.

17. The cosmetic/dermatological composition as defined by claim 13, formulated a cream-gel.

18. The cosmetic/dermatological composition as defined by claim 14, comprising, in water:
   from 0.1% to 0.3% of at least one naphthoic acid compound;
   from 1% to 10% of one or more polyurethane polymers;
   from 0.1% to 3% of gelling agents;
   from 0.01% to 1.5% of chelating agents;
   from 1% to 10% of a wetting agent; and
   from 0.01% to 3% of preservatives.

19. The cosmetic/dermatological composition as defined by claim 13, formulated as a cream, a lotion or a cream-gel, comprising in water:
   from 0.1% to 0.3% of at least one naphthoic acid compound;
   from 1% to 10% of one or more polyurethane polymers;
   from 0.1% to 3% of gelling agents or suspending agents;
   from 0.01% to 1.5% of chelating agents;
   from 1% to 10% of a wetting agent;
   from 0.1% to 20% of an emollient;
   from 0.1% to 30% of fatty phase;
   from 0.01% to 3% of preservatives;
   from 0 to 10% of emulsifiers.

20. The cosmetic/dermatological composition as defined by claim 19, formulated as a lotion, comprising in water:
   about 0.1% of at least one naphthoic acid compound;
   about 3% of one or more polyurethane polymers;
   about 0.2% of gelling agents or suspending agents;
   about 0.1% of chelating agents;
   from 2% to 6% of a wetting agent;
   from 0.1% to 20% of an emollient;
   about 7% of fatty phase;
   from 1% to 1.5% of preservatives;
   from 4% to 6% of emulsifiers.

21. The cosmetic/dermatological composition as defined by claim 1, formulated as a medicament.

22. A process for preparing a cosmetic/dermatological composition as defined by claim 1, comprising mixing a physiologically acceptable vehicle containing at least one naphthoic acid compound with at least one polyurethane polymer, said at least one naphthoic acid compound being dispersed in undissolved form therein.

23. The process as defined by claim 22, comprising the following steps:
   a) mixing the at least one naphthoic acid compound with at least one wetting agent, at least one chelating agent, at least one gelling agent, optionally hydrophilic emulsifiers and emollients, in water, until said at least one naphthoic acid compound is fully dispersed in undissolved form, to obtain an aqueous active phase;
   b) optionally, to produce an emulsion, mixing at least lipophilic emulsifiers, oils and/or solid fatty substances with preservatives, to obtain a fatty phase;
   c) optionally, introducing said fatty phase obtained in b) into the aqueous active phase obtained in a) to obtain an emulsion;
   d) if necessary, introducing a gelling-agent neutralizer into the emulsion obtained in c) or into the aqueous phase obtained in a) to obtain the desired pH, and adding the remaining amount of water; the polyurethane polymer being introduced into the aqueous active phase obtained in a) or into the fatty phase obtained in step b) or during step d) as a function of its lipophilic or hydrophilic nature.

24. The process as defined by claim 22, comprising the following steps:
   step a): preparation of the aqueous active phase:
      introducing purified water, the at least one naphthoic acid compound, optionally hydrophilic emulsifiers in the case of preparing an oil-in-water emulsion, emollients, wetting agents, chelating agent and gelling agent(s) into a beaker with stirring by means of a deflocculator;
      stirring the mixture without heating until fully dispersed wherein the naphthoic acid compound is dispersed in undissolved form;
      when the mixture is homogeneous, adjusting the aqueous phase to 60° C. on a water bath and introducing therein the preservative methyl paraben;
   optional step b): preparation of the fatty phase:
      introducing the lipophilic emulsifiers, oily compounds and preservatives into an additional beaker with stirring by means of a deflocculator;
      adjusting the mixture to 60° C. on a water bath and introducing volatile silicone, if necessary, after homogenization;
   optional step c): emulsification:
   introducing the fatty phase gently into the aqueous phase at a temperature of about 60° C. and with stirring by means of a deflocculator, to effect emulsification;
   continuing heating for 5 minutes, and then allowing the product to cool;
   the stirring being regulated as a function of the viscosity;
   step d): neutralization:
   introducing the gelling-agent neutralizer, if necessary, at about 40° C., up to a pH of 5.5±0.5;
   monitoring the pH and adjusting the volume with water;
   homogenizing and packaging the product;
   the polyurethane polymer being introduced during step a) or during step b) or during step d) as a function of the lipophilic or hydrophilic nature thereof.

25. A method for treating a dermatological condition/affliction associated with a keratinization disorder having a bearing on cell differentiation and proliferation, selected from the group consisting of common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, senile acne, solar acne and medication-related acne, said method comprising administering a cosmetic/dermatological composition as defined by claim 1 to an individual in need of such treatment.

26. The method as defined by claim 25, comprising treating common acne.

27. A method for treating acne-prone skin, for combating the greasy appearance of the skin or the hair, for protection against the harmful effects of sunlight or for the treatment of physiologically greasy skin, or for combating light-induced or chronological aging, said method comprising administering a cosmetic/dermatological composition as defined by claim 1 to an individual in need of such treatment.

28. A method for treating acne, said method comprising administering a cosmetic/dermatological composition as defined by claim 1 to an individual in need of such treatment.

29. The cosmetic/dermatological composition as defined by claim 13, formulated as a cream, a lotion or a cream-gel.

30. The cosmetic/dermatological composition as defined by claim 20, wherein said one or more polyurethane polymers is the polyolprepolymer of type 2.

* * * * *